US006413941B1

United States Patent
Garnett et al.

(10) Patent No.: US 6,413,941 B1
(45) Date of Patent: Jul. 2, 2002

(54) POLYMER COMPOSITION FOR DELIVERING A NUCLEIC ACID OR DERIVATIVE THEREOF

(75) Inventors: Martin Charles Garnett, Derby (GB); Fiona Caroline Maclaughlin, Belfast (IE); Stanley Stewart Davis, Nottingham (GB); Fabio Bignotti, Brescia; Paolo Ferruti, Milan, both of (IT)

(73) Assignee: West Pharmaceutical Services Drug Delivery & Clinical Research Centre Limited, Nottingham (GB)

(*) Notice: Subject to any disclaimer, the term of this patent is extended or adjusted under 35 U.S.C. 154(b) by 0 days.

(21) Appl. No.: 09/101,254

(22) PCT Filed: Jan. 6, 1997

(86) PCT No.: PCT/GB97/00022

§ 371 (c)(1),
(2), (4) Date: Aug. 3, 1998

(87) PCT Pub. No.: WO97/25067

PCT Pub. Date: Jul. 17, 1997

(51) Int. Cl.[7] .............................................. A61K 31/70
(52) U.S. Cl. ..................... 514/44; 424/468; 424/482; 435/320.1; 435/455
(58) Field of Search .................... 424/450, 468, 424/482, 497; 435/455, 320.1, 325; 514/44; 536/23.1

(56) References Cited

U.S. PATENT DOCUMENTS

| | | | |
|---|---|---|---|
| 5,593,658 A | * 1/1997 | Bogdanov et al. | 424/9.34 |
| 5,656,611 A | * 8/1997 | Kabanov | 514/44 |
| 5,717,166 A | * 2/1998 | Tomalia et al. | 424/486 |
| 5,783,178 A | * 7/1998 | Kabanov | 424/78.31 |
| 5,820,873 A | * 10/1998 | Choi et al. | 424/283.1 |
| 5,869,103 A | * 2/1999 | Yeh et al. | 424/501 |

OTHER PUBLICATIONS

Verma et al. (Nature, vol. 389, 18, 239–242), 1997.*
Anderson (Nature, vol. 392, 25–30, 1998.*
Mastrangelo et al., Gene Therapy for Human Cancer: An Essay for Clinicians, Feb. 1996, Seminars in Oncology, vol. 23, No. 1, pp. 4–21.*
Gunzburg et al., Virus vector design in gene therapy, 1995, Molecular Medicine Today, vol. 1, No. 9, pp. 410–417.*
Ledley, Nonviral Gene Therapy: The Promise of Gene as Pharmaceutical Products, Sep. 1995, Human Gene Therapy, vol. 6, pp. 1129–1144.*
Clarenc, et al., "Delivery of antisense oligonucleotides by poly(L–lysine) conjugation and liposome encapsulation," *Anticancer Drug Design* 8: 81–94 (1993).
Crystal, "Transfer of genes to humans: early lessons and obstacles to success," *Science* 270: 404–410 (1995).
Duncan, et al., "A polymer–Triton X–100 conjugate capable of PH–dependent red blood cell lysis: a model system illustrating the possibility of drug delivery within acidic intracellular compartments," *J. Drug Targeting* 2: 341–347 (1994).
Farber, et al., "Optimal conditions for uptake of exogenous DNA by Chinese hamster lung cells deficient in hypoxanthine–guanine phosphoribosyltransferase," *Biochem. Biophys. Acta* 390: 298–311 (1975).
Felgner, et al., "Lipofection: a highly efficient, lipid–mediated DNA–transfection procedure," *Proc. Natl. Acad. Sci. USA* 84: 7413–7417 1987).
Ferruti, et al., "Synthesis, physico–chemical properties and biomedical applications of poly(amido–amine)s," *Polymer* 26: 1336 (1985).
Flory, *Principles of Polymer Chemistry* Cornell University Press: Ithaca, 1953.
Fraley, et al., "Entrapment of a bacterial plasmid in phospholipid vesicles: potential for gene transfer," *Proc. Natl. Acad. Sci. USA* 76: 3348–3352 (1979).
Haensler, et al., "Polyamidoamine cascade polymers mediate efficient transfection of cells in culture," *Bioconjugate Chem.* 4: 372–379 (1993).
Katayose, et al., Salt Lake City Symposium of the Controlled Release Society (Abstract) (1994).
Ledoux, "Uptake of DNA by living cells," *Prog. Nucl. Acid. Res.* 4: 231–267 (1965).
Nucci, et al., "The therapeutic value of poly (ethylene glycol)–modified proteins," *Adv. Drug Del Rev.* 6: 133 (1991).
Plank, et al., "The influence of endosome–disruptive peptides on gene transfer using synthetic virus–like gene transfer systems," *J. Biol. Chem* 269: 12918–12924 (1994).
Ranucci, et al., "A New Synthetic method for Amino–Terminated Poly(ethyleneglycol) Derivatives," *Synthetic Commun.* 20: 2951 (1990).
Ranucci, et al., "Poly(amidoamine)s with potential as drug carriers: degradation and cellular toxicity," *J. Biomater. Sci. Polymer Edn* 2: 303–315 (1991).
Wagner, et al., "Transferrin–polycation conjugates as carriers for DNA uptake into cells," *Proc. Natl. Acad. Sci*USA 87: 3410–3414 (1990).

* cited by examiner

Primary Examiner—Dave T. Nguyen
(74) Attorney, Agent, or Firm—Akin, Gump, Strauss, Hauer & Feld, L.L.P.

(57) ABSTRACT

A composition for delivering a biologically active polyanionic molecule comprising a linear polymer with a backbone comprising amido and tertiary amino groups arranged regularly on the backbone and biologically active polyanionic molecule bound to the polymer. Preferably, the linear polymer comprises a poly(amidoamine). Preferably, the biologically active polyanionic molecule is a nucleic acid, more preferably a DNA. The compositions are useful for delivering nucleic acids to a cell in a cell transformation, transfection or gene therapy method.

36 Claims, 14 Drawing Sheets

GEL SHIFT ASSAY

PLL + 15 mer PS OLIGONUCLEOTIDE IN TBE

*Fig. 1a*

ON: POLYMER RATIO  -VE
ON
8.3
3.3
2.5
1.6
1.1
0.81
0.65
0.33
0.16
0.08
P

ON:POLYMER RATIO  +VE
ON
8.3
3.3
2.5
1.6
1.1
0.81
0.65
0.33
0.16
0.08
P

GEL SHIFT ASSAY

NG23 (BPMP2) + 15 mer PS OLIGONUCLEOTIDE IN TBE

*Fig. 1b*

ON: POLYMER RATIO  -VE
ON
5
2
1.5
1
0.67
0.5
0.4
0.2
0.1
P

ON:POLYMER RATIO  +VE
ON
5
2
1.5
1
0.67
0.5
0.4
0.2
0.1
P

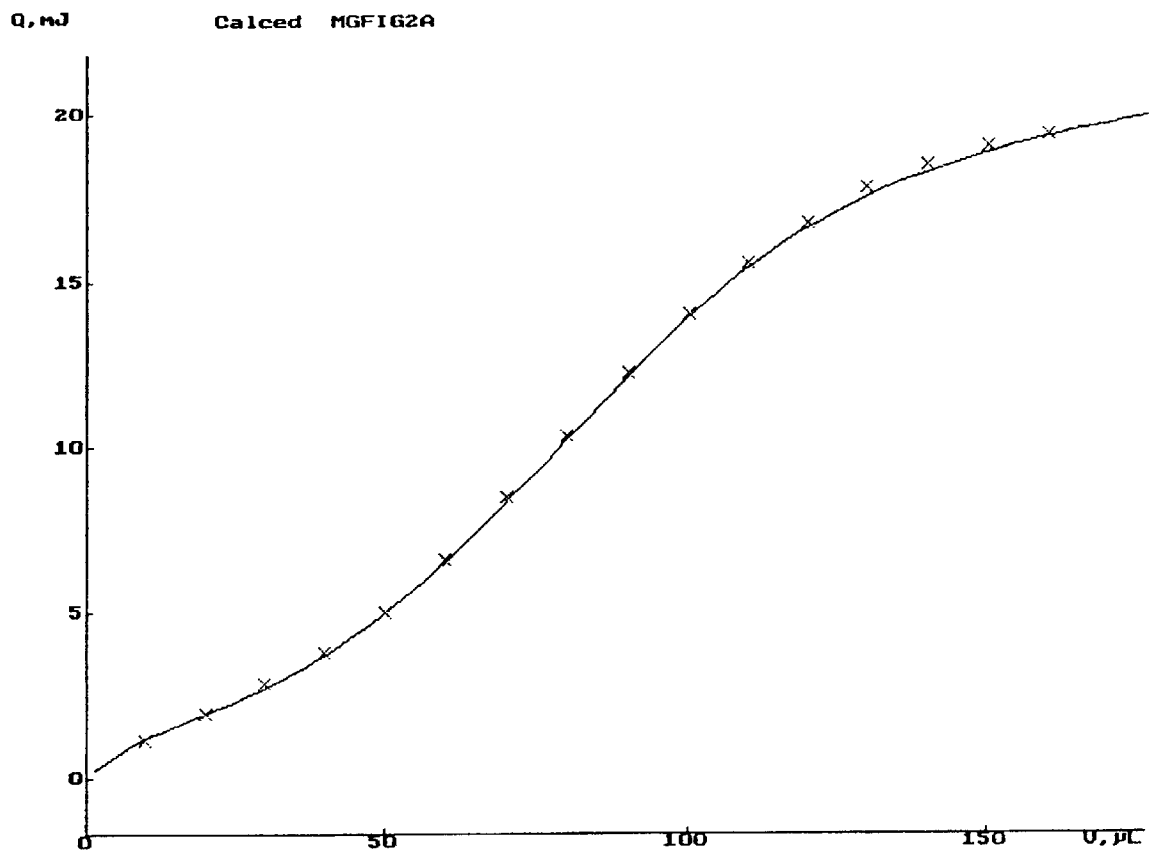
Figure 3a (1 of 2)

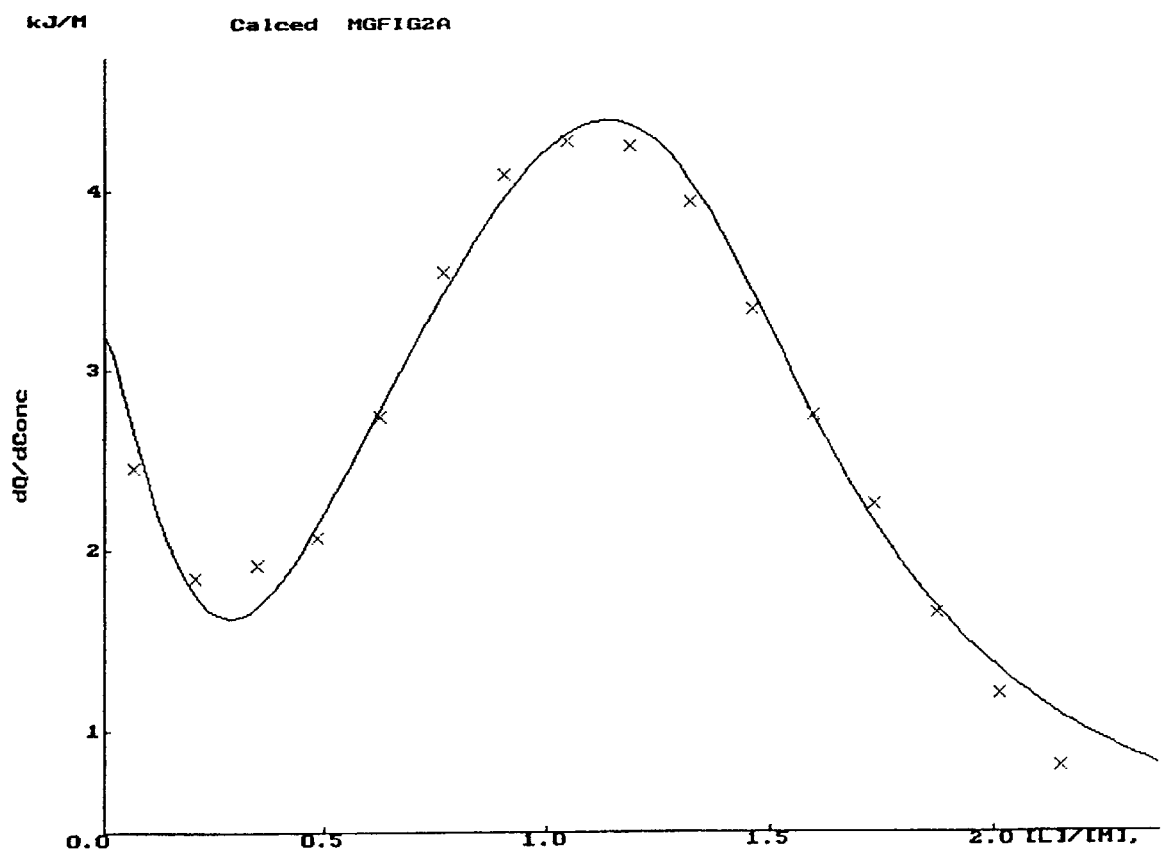
Figure 3a (2 of 2)

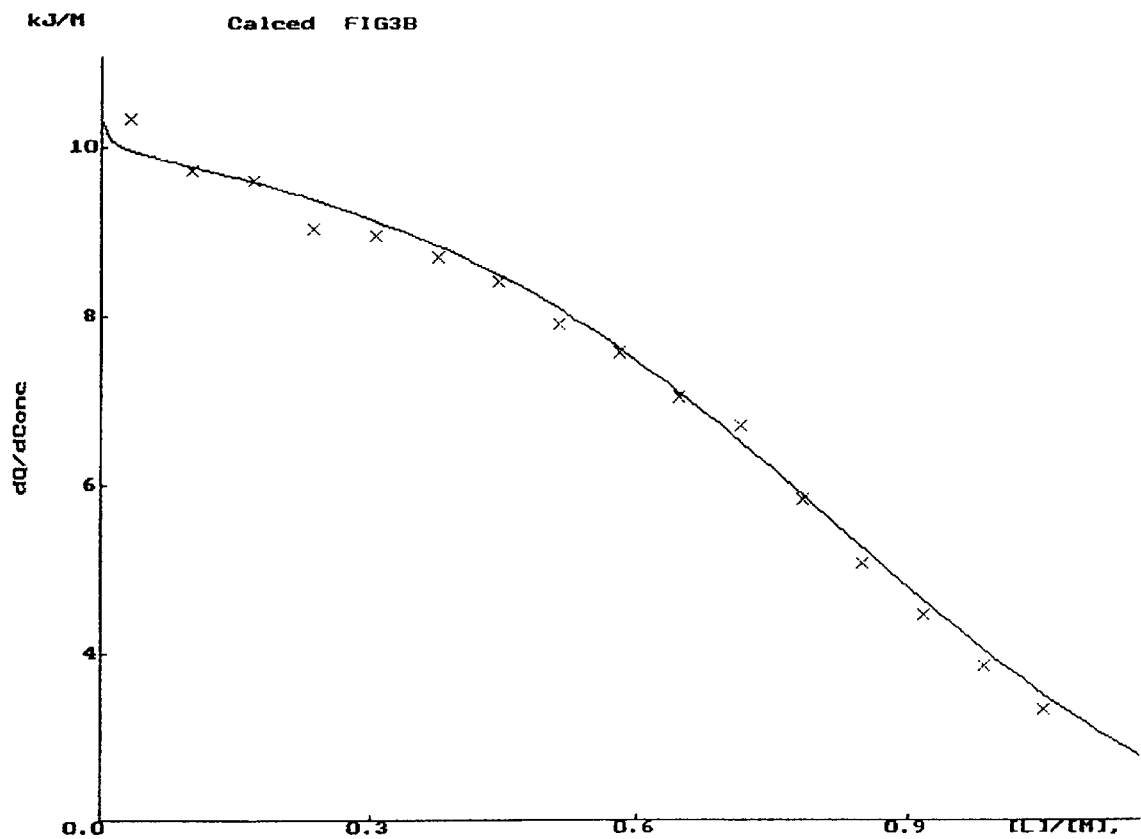
Figure 3b (1 of 2)

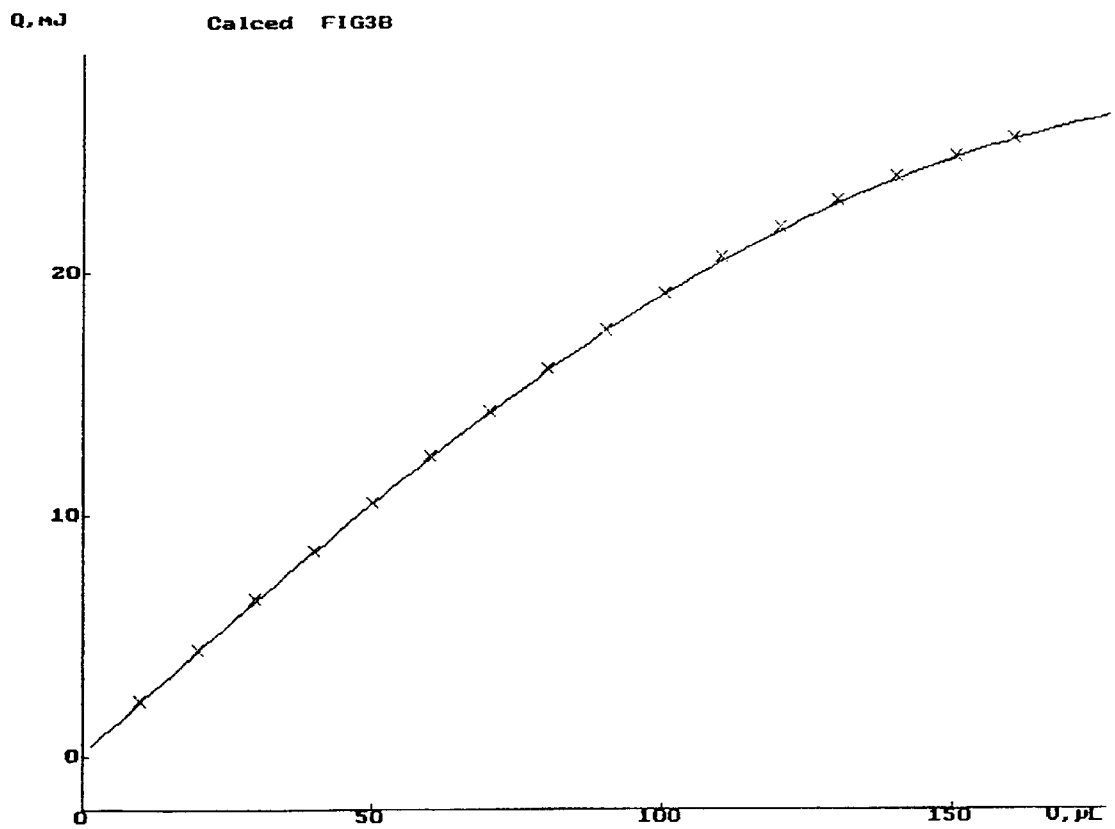
Figure 3b (2 of 2)

GEL SHIFT ASSAY

NG30 (MBA-DMEDA) + 15 mer PS OLIGONUCLEOTIDE IN TBE

ON: POLYMER RATIO           ON:POLYMER RATIO

-VE                         +VE

ON                          ON
1.62                        1.62
0.81                        0.81
0.40                        0.40
0.20                        0.20
0.135                       0.135
0.081                       0.081
0.048                       0.048
P                           P

GEL SHIFT ASSAY

NG32 (BPMP2) PEG-PAA di-block copolymer
+ 15 mer PS OLIGONUCLEOTIDE IN TBE

| ON: POLYMER RATIO | | ON:POLYMER RATIO |
|---|---|---|
| -VE | | +VE |
| ON | | ON |
| 9.1 | | 9.1 |
| 3.7 | | 3.7 |
| 2.9 | | 2.9 |
| 1.27 | | 1.27 |
| 0.94 | | 0.94 |
| 0.75 | | 0.75 |
| 0.38 | | 0.38 |
| 0.19 | | 0.19 |
| 0.09 | | 0.09 |
| P | | P |

GEL SHIFT ASSAY

NG33 (BPMP2) PEP-PAA-PEG triblock copolymer
+ 15 mer PS OLIGONUCLEOTIDE IN TBE

| ON: POLYMER RATIO | | ON:POLYMER RATIO |
|---|---|---|
| -VE | | +VE |
| ON | | ON |
| 14.3 | | 14.3 |
| 5.2 | | 5.2 |
| 4.0 | | 4.0 |
| 2.7 | | 2.7 |
| 1.79 | | 1.79 |
| 1.35 | | 1.35 |
| 1.08 | | 1.08 |
| 0.54 | | 0.54 |
| 0.77 | | 0.77 |
| 0.135 | | 0.135 |
| P | | P |

PLL = poly (L-Lysine)
PAA = Bis acryloyl piperazine-2-methyl piperazine
x = degree of polymerisation

POLYMER COMPOSITION FOR DELIVERING A NUCLEIC ACID OR DERIVATIVE THEREOF

Priority is claimed under 35 U.S.C. §119 to PCT/GB97/00022, filed Jan. 6, 1997, which corresponds to GB 9600272.0, filed Jan. 6, 1996.

The present invention relates to polymers, in particular to polymers for the delivery of nucleic acid to a cell.

For many research applications in genetic manipulation and genetic engineering, it is necessary to express new or modified genes in living cells. However the uptake of DNA into cells is poor resulting in inconsistent expression. Similarly, gene therapy, antisense oligonucleotide therapy and gene vaccination require that DNA and DNA analogues can survive in a hostile biological environment, penetrate biological barriers, be taken up into cells and move to the correct subcellular compartment to exert their therapeutic effects.

The identification of defective genes responsible for disease states, either through the overproduction of key proteins, the production of defective proteins or the defective control of gene production, offers new possibilities for the treatment of disease. By controlling the defect at the genetic level a range of diseases could now be treated effectively rather than by merely treating the symptoms of these diseases. This has been achieved in some cases, or is believed to be achievable, by the expression of new competent genes, or by controlling the overproduction of unwanted gene products or by controlling the expression of genes. These processes could be achieved by the insertion of new DNA or by the administration and uptake of complementary strands of DNA or DNA analogues which inhibit the production or control the production of existing genes [1]. In both of these strategies it is necessary to deliver to the cell sufficient DNA to achieve modified cell expression. The DNA must also be delivered to the correct intracellular compartment to effect that change. While some DNA is taken up naturally into cells, the amount taken up is small and inconsistent, and expression of added DNA is poor. DNA is an inherently unstable material, particularly in a biological environment where many specific enzymes capable of degrading DNA are found [2]. Either for therapeutic purposes, or for expression of new or modified genes for research purposes, a more efficient and reliable method of delivering DNA is required and, in particular, protection of the DNA against metabolic effects is highly desirable.

A number of strategies have been proposed to achieve these aims. These include the use of liposomes [3], cationic lipids [4], which are often incorrectly referred to as 'cationic liposomes', and the use of cationic polymers such as polylysine [5] or polyornithine as DNA delivery agents.

Both oligonucleotides and DNA constructs, such as plasmids, have shown improved activity by condensation with polycations such as polylysine. In the former case chemical conjugation of oligonucleotide to the polymer is required, whereas in the latter case complexation of polymer with DNA also confers these effects. Poly-L-lysine (PLL) is believed to condense the DNA into a smaller volume, and by the excess positive charge of the complex, bind to negatively charged cell surfaces to facilitate interaction with the cell surface and uptake into the cell.

The effectiveness of polylysine-DNA complexes has been enhanced by coupling ligands to the polylysine which further facilitate binding and uptake into cells [6]. Membrane destabilising agents have been added to DNA preparations to facilitate exit of the DNA from the degradative endosomal compartments of the cell [7].

To date, few different cationic polymers have been used in this work, and the available polymers are deficient in a number of respects. Poly-L-lysine, the principal polymer presently used for this purpose, is known to be toxic above a small molecular weight [8], it does not interact stoichiometrically with DNA, and the resulting complex is unreliable, difficult to control and its properties strongly dependent on the ratio of DNA to polymer.

Ranucci et al [15] describes the synthesis of poly (amidoamine)s and suggests their use as polymeric drug carriers using covalent attachment of the drug molecule to the polymer.

Ranucci and Ferruti [12] describes hydrolyzable block copolymers containing poly(ethyleneglycol) (PEG) and poly (amidoamine) (PAA) or poly(amido-thioether-amine).

Haensler and Szoka [10] suggests that polyamidoamine cascade polymers (dendrimers prepared from branched chain poly(amidoamine)s) of a certain size may be useful in transfection of cells in culture and states that linear polycations in general are relatively cytotoxic and by themselves not very efficient, which limits their usefulness for transfection of cells in culture.

Duncan et al [16] describes poly(amidoamine)-Triton X-100 conjugates which may be useful for drug delivery.

Katayose and Kataoka [17] suggest that a PEG-poly (lysine) block copolymer as a potential DNA delivery system.

Attaching PEG chains to macromolecules and colloidal particles has been described for many biomedical products [11].

There remains a need for polymers which have improved properties for use in DNA delivery systems.

A first aspect of the invention provides a composition for delivering a biologically active polyanionic molecule, the composition comprising a linear polymer with a backbone comprising amido and tertiary amino groups arranged regularly on the said backbone and said biologically active polyanionic molecule bound to said polymer.

The said linear polymers are cationic and, depending on their nature, as discussed more fully below, the polymers have a range of physicochemical properties.

Conveniently, the said linear polymer comprises a poly (amidoamine) (PAA). Suitably, said linear polymer consists of a poly(amidoamnine). PAAs are degradable in water since they contain hydrolyzable amidic bonds in their main chain together with nucleophilic tertiary-aminic fuinctions in the position. The polymers can be synthesised from a wide variety of primary monoamines or secondary bisamines which enable full control to be exercised over the spacing and pKa of the cationic groups [9] for optimisation of the interaction with a suitable biologically active polyanionic molecule. Preferably, PAAs are water soluble, and thus facilitate the solubility of the complex. Further solubilisation of complexes can be achieved by use of the copolymers containing hydrophilic PEG chains. (Reference [9] is incorporated herein by reference.)

It is preferred if the pKa of the cationic groups is between 7 and 8. It has been found that PAA with a low pKa binds DNA less well than PAA with a high pKa. It is more preferred if the pKa of the PAA is around 8.

Thus, in a preferred embodiment, said linear polymer further comprises ethylene glycol or poly(ethyleneglycol). It is particularly preferred if the linear polymer is a poly (ethyleneglycol)-poly(amidoamine) block copolymer or ethyleneglycol-poly(amidoamine) block copolymer.

Preferably said linear polymer is a block copolymer with the structure $[poly(amidoaniine)\text{-}(ethyleneglycol)_y]_x$ wherein x is from 1 to 50 and y is from 1 to 200, wherever it may occur.

Also preferably said linear polymer is a block copolymer with the structure (ethyleneglycol)$_y$-poly(amidoamine)-(ethyleneglycol)$_y$ wherein each y is independently 1 to 200.

Suitably the linear polymer consists of or comprises a PAA which has the formula:

(a)
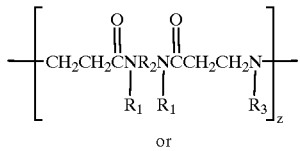

or (b)
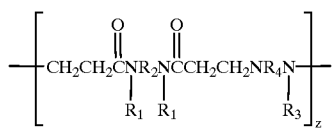

or said linear polymer comprises a PAA such as with the formula:

(c)
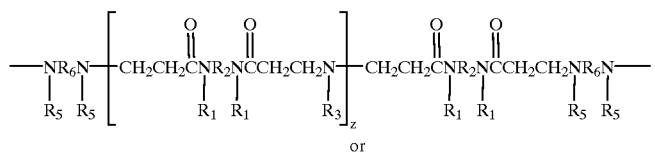

or (d)
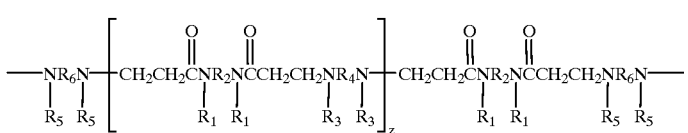

or (e) wherein

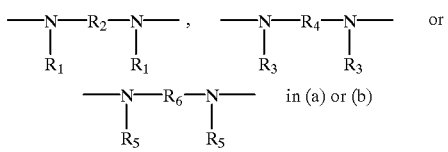

are replaced by

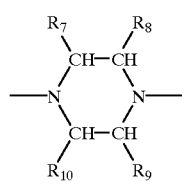

and, in any case, z is from 0 (or 1 as appropriate) to 70 and each $R_1$ is independently H or a linear or branched hydrocarbon chain —$C_nH_{2n+1}$ with n=1–4 whenever it occurs; each $R_2$ is independently a linear or branched alkylene chain —$C_nH_{2n}$— with n=1–4 whenever it occurs; each $R_3$ is independently a linear or branched hydrocarbon chain —$C_nH_{2n+1}$ with n=1–4 whenever it occurs; each $R_4$ is independently a linear or branched alkylene chain —$C_nH_{2n}$— with n=2–4 whenever it occurs; each $R_5$ is independently a linear or branched hydrocarbon chain —$C_nH_{2n+1}$ with n=1–4; each $R_6$ is independently a linear or branched alkylene chain —$C_nH_{2n}$— with n=2–4; and wherein $R_7$, $R_8$, $R_9$ and $R_{10}$ are independently H or linear or branched hydrocarbon chain —$C_nH_{2n+1}$ with n=1–3 whenever they occur.

Preferably Z is from 30 to 70.

It is preferred if the $M_n$ of the PAA is greater than 10 000; more preferably greater than 15 000.

Conveniently the linear polymer has the formula:

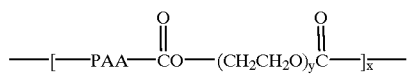

wherein PAA has the formula as defined above, x is from 1 to 50 and y is from 1 to 200.

Preferably, the linear polymer has the formula $$CH_3O-(-CH_2CH_2O)_y-\overset{O}{\underset{\|}{C}}-PAA-\overset{O}{\underset{\|}{C}}-O(-CH_2CH_2O)_y-CH_3$$

wherein PAA has the formula as defined above and y is from 1 to 200. The preferences for the degree of polymerisation of the PAA in the PAA-PEG copolymers is the same as for the PAA polymers (ie preferably Z is from 30 to 70).

The biologically active polyanionic molecule may be any suitable such molecule but preferably said molecule comprises a regular array of negative charges.

It is preferred if the molecule comprising a regular array of negative charges is a nucleic acid or a derivative thereof.

It is less preferred if the molecule is heparin.

The nucleic acid or derivative thereof may be DNA or RNA.

The nucleic acid may be an antisense nucleic acid. The nucleic acid is conveniently an oligonucleotide such as an antisense oligonucleotide.

If the molecule is an oligonucleotide it is preferred that the PAA has a relatively low degree of polymerisation. If the molecule is a larger DNA or RNA molecule it is preferred that the PAA has a relatively high degree of polymerisation.

The nucleic acid, as discussed below, is preferably a therapeutic nucleic acid useful in gene therapy, nucleic acid vaccination, antisense therapy and the like. As discussed in more detail below, the nucleic acid may comprise natural (phosphate) phosphodiester linkages or it may comprise non-natural linkages such as those including phosphorothioates. It is preferred if the nucleic acid is DNA or a derivative thereof.

Antisense oligonucleotides are single-stranded nucleic acid, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise sequence-specific molecules which specifically bind double-stranded DNA via recognition of major groove hydrogen binding sites.

Clearly, the sequence of the antisense nucleic acid or oligonucleotide can readily be determined by reference to the nucleotide sequence of the gene whose function is to be interfered with.

In a still further embodiment the nucleic acid delivered to a target cell encodes an antisense RNA.

An antisense RNA includes an RNA molecule which hybridises to, and interferes with the expression from a MRNA molecule encoding a protein or to another RNA molecule within the cell such as pre-mRNA or tRNA or rRNA, or hybridises to, and interferes with the expression from a gene.

Conveniently, a gene expressing an antisense RNA may be constructed by inserting a coding sequence encoding a protein adjacent a promoter in the appropriate orientation such that the RNA complementary to MRNA. Suitably, the antisense RNA blocks expression of undesirable polypeptides such as oncogenes, for example ras, bcl, src or tumour suppressor genes such as p53 and Rb.

It will be appreciated that it may be sufficient to reduce expression of the undesirable polypeptide rather than abolish the expression.

It will be further appreciated that DNA sequences suitable for expressing as antisense RNA and for designing other antisense nucleic acids may be readily derived from publicly accessible databases such as GenBank and EMBL.

Oligonucleotides are subject to being degraded or inactivated by cellular endogenous nucleases. To counter this problem, it is possible to use modified oligonucleotides, eg having altered internucleotide linkages which retain a negative charge, in which the naturally occurring phosphodiester linkages have been replaced with another linkage. For example, Agrawal et al (1988) *Proc. Natl. Acad. Sci. USA* 85, 7079–7083 showed increased inhibition in tissue culture of HIV-1 using oligonucleotide phosphoramidates and phosphorothioates. Agrawal et al (1989) *Proc. Natl. Acad. Sci. USA* 86, 7790–7794 showed inhibition of HIV-1 replication in both early-infected and chronically infected cell cultures, using nucleotide sequence-specific oligonucleotide phosphorothioates. Leither et al (1990) *Proc. Natl. Acad. Sci. USA* 87, 3430–3434 report inhibition in tissue culture of influenza virus replication by oligonucleotide phosphorothioates.

Oligonucleotides having artificial linkages have been shown to be resistant to degradation in vivo. For example, Shaw et al (1991) in *Nucleic Acids Res.* 19, 747–750, report that otherwise unmodified oligonucleotides become more resistant to nucleases in vivo when they are blocked at the 3' end by certain capping structures and that uncapped oligonucleotide phosphorothioates are not degraded in vivo.

A detailed description of the H-phosphonate approach to synthesizing oligonucleos dephosphorothioates is provided in Agrawal and Tang (1990) *Tetrahedron Letters* 31, 7541–7544, the teachings of which are hereby incorporated herein by reference. Syntheses of oligonucleoside phosphorodithioates and phosphoramidates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemistry* 27, 7237; Uznanski et al (1987) *Tetrahedron Letters* 28, 3401; Bannwarth (1988) *Helv. Chim. Acta.* 71, 1517; Crosstick and Vyle (1989) *Tetrahedron Letters* 30, 4693; Agrawal et al (1990) *Proc. Natl. Acad. Sci. USA* 87, 1401–1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesized and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulphur in the linkage. The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res.* 19, 747–750 and Agrawal et al (1991) *Proc. Natl. Acad. Sci. USA* 88(17), 7595–7599, the teachings of which are hereby incorporated herein by reference.

A further method of making oligonucleotides resistant to nuclease attack is for them to be "self-stabilized" as described by Tang et al (1993) *Nucl. Acids Res.* 21, 2729–2735 incorporated herein by reference. Self-stabilized oligonucleotides have hairpin loop structures at their 3' ends, and show increased resistance to degradation by snake venom phosphodiesterase, DNA polymerase I and fetal bovine serum. The self-stabilized region of the oligonucleotide does not interfere in hybridization with complementary nucleic acids, and pharmacokinetic and stability studies in mice have shown increased in vivo persistence of self-stabilized oligonucleotides with respect to their linear counterparts.

It is preferred that the oligonucleotides contain phosphodiester linkages.

However, the polymers of the invention can aid compaction and stabilisation of the nucleic acid and, it is believed, can protect the nucleic acid from degradation.

We have found that this family of cationic polymers, and the complexes formed, have superior properties for use as DNA delivery systems in comparison with other cationic polymers previously reported for this purpose.

Complexes between the polymers as defined, and in particular polyamidoamines and copolymers thereof, and DNA are readily formed by simple mixing at the required ratio of DNA to polymer. In contrast to complexes of poly-L-lysine and DNA, which are invariably insoluble and form colloidal particles in the size range of 100 nm to several $\mu$m in diameter, the PAA-DNA complexes remain soluble under some conditions.

The use of PEG containing polymers increase the range of conditions under which soluble complexes are seen. Generally PEGylation has the effect of reducing interaction with scavenger receptors and cells, so prolonging the circulation half-life and reducing immunogenic responses. In the case of complexes with DNA this is also expected to reduce the metabolism of DNA by serum enzymes. The advantages of having the PEG bound to the polymer rather than directly to the DNA is that it reduces the possibility that the hydrophilic PEG will interfere with the uptake of DNA into the cell through hydrophobic membranes and hence location to the correct intracellular compartment. The synthesis of PAA and PAA-PEG, however still allows for the further conjugation of other biologically active recognition sequences to further improve the uptake of the DNA and its transfer to the correct intracellular compartment.

A preferred embodiment is wherein the polymer further comprises a biologically active recognition signal. The said signal may aid the targeting, uptake or intracellular localisation of the composition and therefore the said biologically active polyanionic molecule.

Suitable said recognition signals include ligands for binding and endocytosis especially of DNA delivery systems such as transferrin, for example see E. Wagner, M. Cotten, R. Foisner and M. L. Bernstiel (1991) *Proc. Natl. Acad. Sci. USA* 88, 4255–4259; carbohydrate residues, for example galactose, or mannose residues to target to hepatocytes or macrophages respectively. (G. Ashwell and J. Harford (1982) *Ann. Rev. Biochem.* 51, 531–54 describes carbohydrate specific receptors of the liver and use of asialoglycoprotein receptor in gene targeting with attachment of asialo-orosomucoid to PLL-DNA constructs is described in G. Y. Wu and C. H. Wu (1988) *Biochemistry* 27, 887–892.); folate receptors as described in C. P. Leamon and P. S. Low (1991) *Proc. Natl. Acad. Sci. USA* 88, 5572–5576 and G. Citro, C. Szczylik, P. Ginobbi, G. Zupi and B. Calabretta (1994) *Br. J. Cancer* 69, 463–464; monoclonal antibodies, especially those selective for a cell-surface antigen; and any other ligand which will mediate endocytosis of macromolecules.

Monoclonal antibodies which will bind to many of these cell surface antigens are already known but in any case, with today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in *"Monoclonal Antibodies: A manual of techniques"*, H Zola (CRC Press, 1988) and in *"Monoclonal Hybridoma Antibodies: Techniques and Applications"*, J G R Hurrell (CRC Press, 1982).

Chimaeric antibodies are discussed by Neuberger et al (1988, 8th International Biotechnology Symposium Part 2, 792–799).

Suitably prepared non-human antibodies can be "humanized" in known ways, for example by inserting the CDR regions of mouse antibodies into the framework of human antibodies.

Suitable endosome disrupting agents such as viral fusogenic peptides and adenoviral particles have been described in J-P. Bongartz, A-M. Aubertin, P. G. Milhaud and B. Lebleu (1994) *Nucleic Acids Research* 22, 4681–4688 and M. Cotten, E. Wagner, K. Zatloukal, S. Phillips, D. T. Curiel, M. L. Bernstiel (1992) *Proc. Natl. Acad. Sci. USA* 89, 6094–6098.

All of these journal articles are incorporated herein by reference.

Complexes have been formed between polymers and short single stranded DNA with both phosphodiester and phosphorothioate backbones, and high molecular weight double stranded DNA. The complexes formed have been characterised by microcalorimetry, DNA melting profiles, gel-shift electrophoresis and photon correlation spectroscopy.

It is most preferred if the biologically active polyanionic molecule is a therapeutic molecule such as a therapeutic nucleic acid.

Therapeutic nucleic acids include any nucleic acid that it is useful to deliver to a patient, and includes nucleic acid vaccines.

Preferably the nucleic acid is suitable for gene therapy.

In one embodiment, the nucleic acid encodes a molecule having a directly or indirectly cytotoxic function. By "directly or indirectly" cytotoxic, we mean that the molecule encoded by the gene may itself be toxic (for example ricin; tumour necrosis factor; interleukin-2; interferon-gamma; ribonuclease; deoxyribonuclease; Pseudomonas exotoxin A) or it may be metabolised to form a toxic product, or it may act on something else to form a toxic product. The sequence of ricin cDNA is disclosed in Lamb et al (1985) *Eur. J. Biochem.* 148, 265–270 incorporated herein by reference.

For example, it would be desirable to deliver to cancer cells within a patient a nucleic acid encoding an enzyme using the compositions of the invention, the enzyme being one that converts a relatively non-toxic prodrug to a toxic drug. The enzyme cytosine deaminase converts 5-fluorocytosine (5FC) to 5-fluorouracil (5FU) (Mullen et al (1922) *PNAS* 89, 33); the herpes simplex enzyme thymidine kinase sensitises cells to treatment with the antiviral agent ganciclovir (GCV) or aciclovir (Moolten (1986) *Cancer Res.* 46, 5276; Ezzedine et al (1991) *New Biol* 3, 608). The cytosine deaminase of any organism, for example *E. coli* or *Saccharonzyces cerevisiae*, may be used.

Thus, in one embodiment of the invention, the nucleic acid encodes a cytosine deaminase and the patient is concomitantly given 5FC. By "concomitantly", we mean that the 5FC is administered at such a time, in relation to the transformation of the tumour cells, that 5FC is converted into 5FU in the target cells by the cytosine deaminase expressed from the said gene. A dosage of approximately 0.001 to 100.0 mg 5FC/kg body weight/day, preferably 0.1 to 10.0 mg/kg/day is suitable.

Components, such as 5FC, which are converted from a relatively non-toxic form into a cytotoxic form by the action of an enzyme are termed "pro-drugs".

In a further embodiment the nucleic acid delivered to the target cell is or encodes a ribozyme capable of cleaving targeted RNA or DNA. The targeted RNA or DNA to be cleaved may be RNA or DNA which is essential to the function of the cell and cleavage thereof results in cell death or the RNA or DNA to be cleaved may be RNA or DNA which encodes an undesirable protein, for example an oncogene product, and cleavage of this RNA or DNA m ay prevent the cell from becoming cancerous.

Ribozymes which may be encoded in the genomes of the viruses or virus-like particles herein disclosed are described in Cech and Herschlag "Site-specific cleavage of single stranded DNA" U.S. Pat. No. 5,180,818; Altaa et al "Cleavage of targeted RNA by RNAse P" U.S. Pat. No. 5,168,053, Cantin et al "Ribozyme cleavage of HW-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods, U.S. Pat. No. 5,093, 246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

In another embodiment of the invention, the nucleic acid replaces the function of a defective gene in the target cell.

There are several thousand inherited genetic diseases of mammals, including humans, that are caused by defective genes. Examples of such genetic diseases include cystic fibrosis, where there is known to be a mutation in the CFTR gene; Duchenne muscular dystrophy, where there is known to be a mutation in the dystrophin gene; sickle cell disease, where there is known to be a mutation in the HbA gene. Many types of cancer are caused by defective genes, especially protooncogenes, and tumour-suppressor genes that have undergone mutation.

The following table shows current targets for gene therapy.

| Diseases caused by single gene defects: current targets for gene therapy | |
|---|---|
| Disease | Defective gene |
| Immunodeficiency | Adenosine deaminase |
|  | Purine nucleoside phosphorylase |
| Hypercholesterolaemia | LDL receptor |
| Haemophilia | Factor IX |
|  | Factor VIII |
| Gaucher's disease | Glucocerebrosidase |
| Mucopolysaccharidosis | β-glucuronidase |
| Emphysema | α1-antitrypsin |
| Cystic fibrosis | Cystic fibrosis transmembrane regulator |
| Phenylketonuria | Phenylalanine hydroxylase |
| Hyperammonaemia | Ornithine transcarbamylase |
| Citrullinaemia | Arginosuccinate synthetase |
| Muscular dystrophy | Dystrophin |
| Thalassaemia | β-globin |
| Sickle cell anaemia | β-globin |
| Leukocyte adhesion deficiency | CD-18 |

This list indicates the principal current targets for gene therapy. Many of the diseases listed can be caused by defects in more than one gene; the gene defect listed is the defect targeted by current research.

Thus, it is preferred that the composition of the invention, which may be useful in the treatment of cystic fibrosis, contains a functional CFTR gene to replace the function of the defective CFTR gene. Similarly, it is preferred that the virus or virus-like particle of the invention, which may be useful in the treatment of cancer, contains a functional protooncogene, or tumour-suppressor gene to replace the function of the defective protooncogene or tumour-suppressor gene.

Examples of protooncogenes are ras, src, bcl and so on; examples of tumour-suppressor genes are p53 and Rb.

The nucleic acid may contain introns, or it may be a gene or a fragment thereof, or cDNA, or fragment thereof.

Nucleic acids suitable for use in vaccines of the present invention include those described in Volume 12(16) of Vaccine which is a special conference issue of the WHO meeting on nucleic and vaccines, and is incorporated herein by reference. Nucleic acid vaccines for tuberculosis, influenza, hepatitis B, Leishmaniasis and HIV have been considered.

The nucleic acid, especially DNA, which is bound to the polymer in the composition of the invention may be any suitable size. Preferably the nucleic acid is from 10 to 10 million bases or base pairs. Suitably oligonucleotides are from 10 bases to 200 bases, more suitably 10 bases to 100 bases.

Conveniently RNA and DNA molecules are from 100 to 1 million bases or base pairs.

More preferably the nucleic acid is from 20 to 1 million bases or base pairs, still more preferably the nucleic acid is from 1000 to 500,000 bases or base pairs and most preferably the nucleic acid is from 5000 to 150,000 bases or base pairs.

The nucleic acid may conveniently be plasmid DNA whether supercoiled, open circle or linearised plasmid DNA.

It is believed that the nucleic acid binds to the polymer non-covalently.

A second aspect of the invention provides a composition according to the first aspect of the invention for use in medicine.

A third aspect of the invention provides a composition according to the first aspect of the invention in the manufacture of a medicament for treatment of a disease.

A fourth aspect of the invention provides a pharmaceutical composition comprising a composition according to the first aspect of the invention and a pharmaceutically effective carrier.

The formulations may conveniently be presented in unit dosage form and may be prepared by any of the methods well known in the art of pharmacy. Such methods include the step of bringing into association the active ingredient (composition of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

A fifth aspect of the invention provides a method of making a composition according to the first aspect of the invention comprising contacting said biologically active polyanionic molecule with said linear polymer.

Preferably, the biologically active polyanionic molecule and the said linear polymer are simply mixed together, preferably in solution, more preferably in aqueous solution. They may be mixed together quickly or slowly. Preferably, the biologically active polyanionic molecule is a nucleic acid, more preferably DNA.

When nucleic acid is used, it is convenient to mix the nucleic acid and polymer in a high salt solution and dialyse against water. This method is particularly preferred for large nucleic acid molecules such as those >1 kb. It is also convenient to heat the mixture of polymer and nucleic acid and to cool the mixture slowly. Preferably, the mixture is a solution, more preferably an aqueous solution.

A sixth aspect of the invention provides a method of delivering a biologically active polyanionic molecule to a host, the method comprising administering to said host an effective amount of a composition according to the first aspect of the invention.

The host is suitably a patient to be treated with the biologically active polyanionic molecule.

The host may be, for example, a cell in culture in vitro or it may be an experimental animal.

Preferably, the biologically active polyanionic molecule is a nucleic acid, more preferably DNA.

When the host is a cell in culture the method can be used to transfect or transform the cell with the nucleic acid, preferably DNA.

A seventh aspect of the invention provides a method of delivering a biologically active polyanionic molecule to a cell in an environment, the method comprising administering to said environment a composition as defined in the first aspect of the environment.

The environment may be a patient to be treated or an experimental animal to be treated or a culture medium containing cells.

Preferably the environment is a culture medium containing cells. When the biologically active polyanionic molecule is a nucleic acid the cells may be transfected or transformed using this method by administering a suitable composition to the culture medium.

By "cells" we include both prokaryotic and eukaryotic cells. Thus, the cells include cells of bacteria, yeast, fungi, plants, vertebrates (such as mammalian cells) and invertebrates (such as insect cells).

Preferably the nucleic acid to be delivered is DNA.

Preferably in this method the said composition is contacted with said cell.

Preferably for the methods described in the fifth, sixth and seventh aspects of the invention the biologically active polyanionic molecule is a therapeutic molecule and more preferably the therapeutic molecule comprises a nucleic acid.

An eighth aspect of the invention provides a method of treating, preventing or ameliorating a disease in a multicellular organism which multicellular organism benefits from the administration of a biologically active polyanionic molecule, the method comprising administering to the patient a composition as defined in the first aspect of the invention.

Preferably the biologically active polyanionic molecule comprises a therapeutic nucleic acid or derivative thereof.

The multicellular organism may be an animal or human or a plant, preferably an animal especially a mammal and more preferably a human.

The animal or human is therefore a patient.

The aforementioned compositions may be administered to the plant in any suitable way.

The aforementioned compositions of the invention or a formulation thereof may be administered to the patient by any conventional method including oral and parenteral (eg subcutaneous or intramuscular) injection. The treatment may consist of a single dose or a plurality of doses over a period of time.

Whilst it is possible for a composition of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline or buffered solutions preferably wherein the buffer buffers in a physiological pH range which will be sterile and pyrogen free.

A ninth aspect of the invention provides a polymer with the formula (ethylene glycol)$_y$-poly(amidoamine)-(ethyleneglycol)$_y$ wherein each y is independently from 1 to 200.

Preferably the compound has the formula

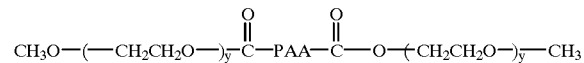

wherein PAA is a poly(amidoamine) as defined above and each y is independently from 1 to 200.

This polymer can be used as the polymer in all previous aspects of the invention and it may also be useful in binding drugs generally for delivery to a patient to be treated.

The invention will now be described in more detail with respect to the following Figures and Examples wherein:

FIGS 1A and 1B show a gel-shift assay comparing the interaction of (a) poly-L-lysine and (b) PAA with phosphorothioate oligonucleotide (15 mer) at various oligonucleotide:polymer ratios (the abbreviation ON means oligonucleotide, and the abbreviation P means polymer whenever it occurs in the Figures relating to gels);

Figure 4:
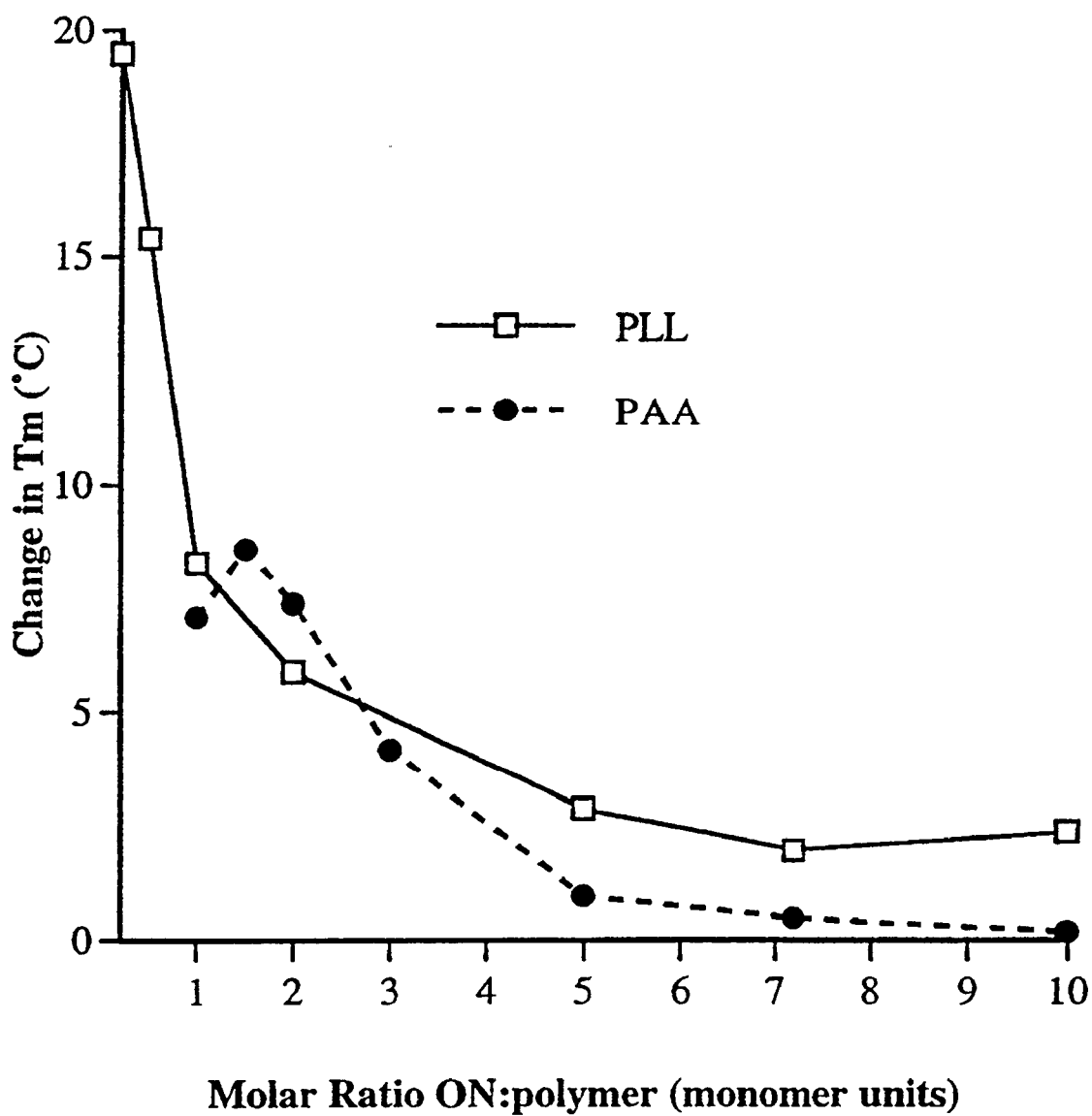
Figure 5:
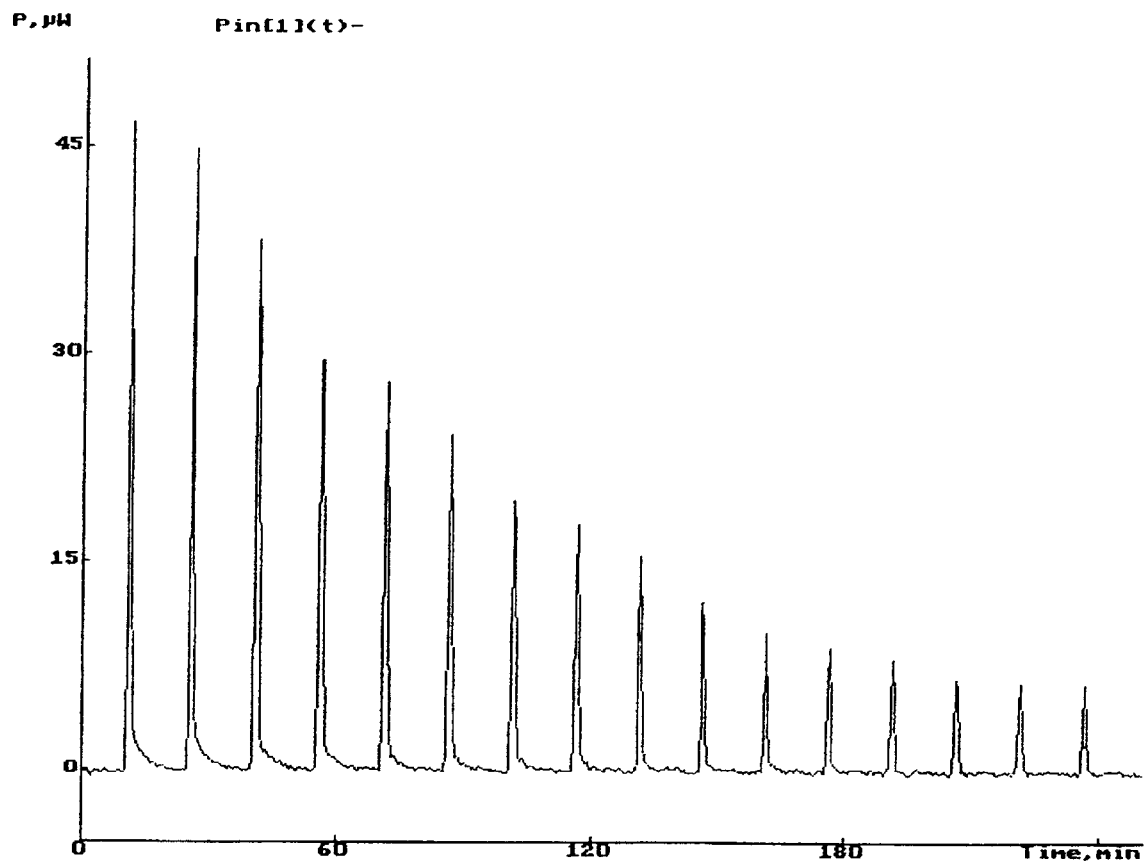
Figure 6:
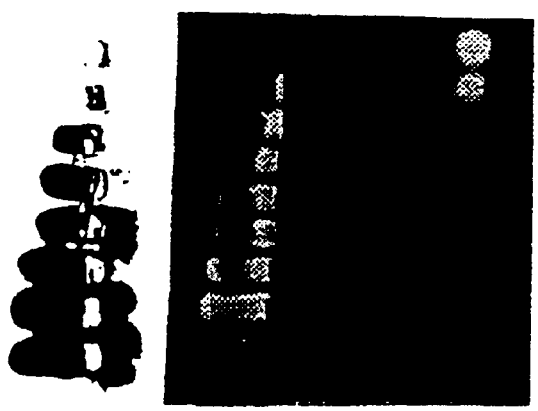
Figures 7A, 7B:
Figure 8A:
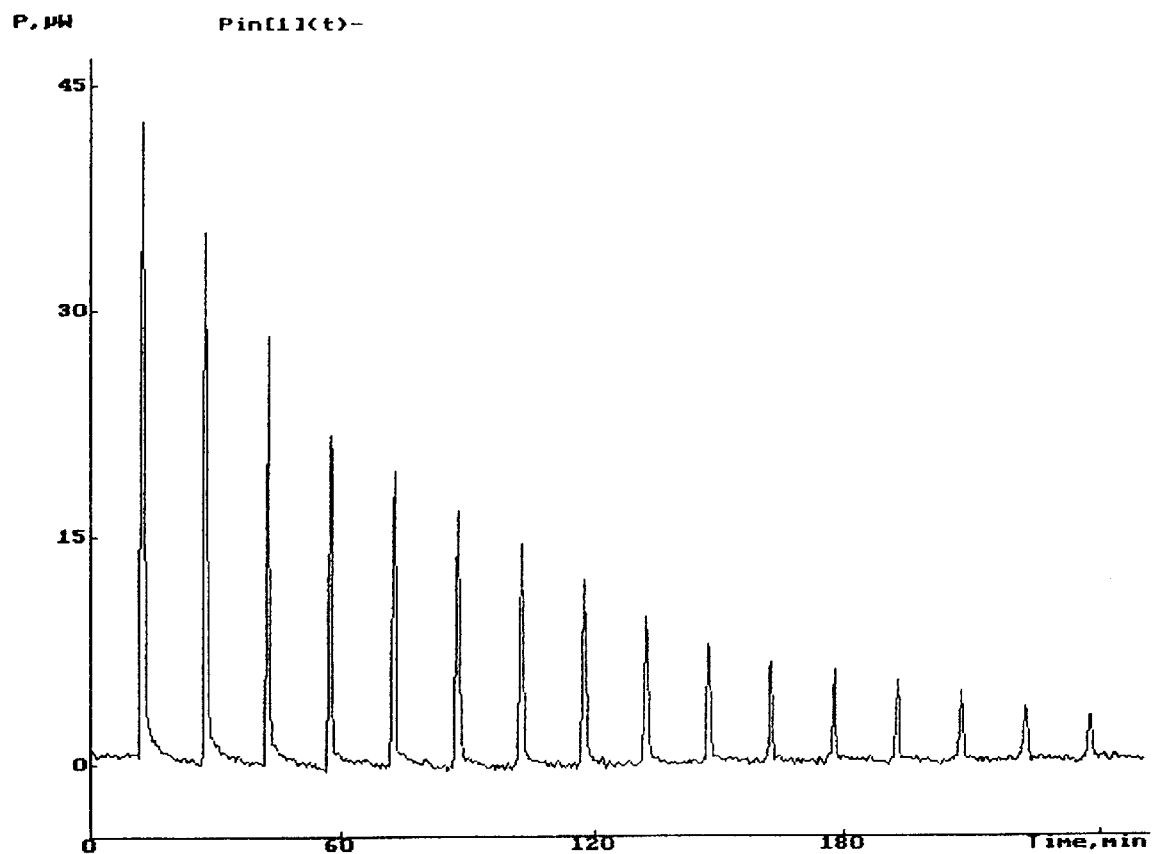
Figure 8B:
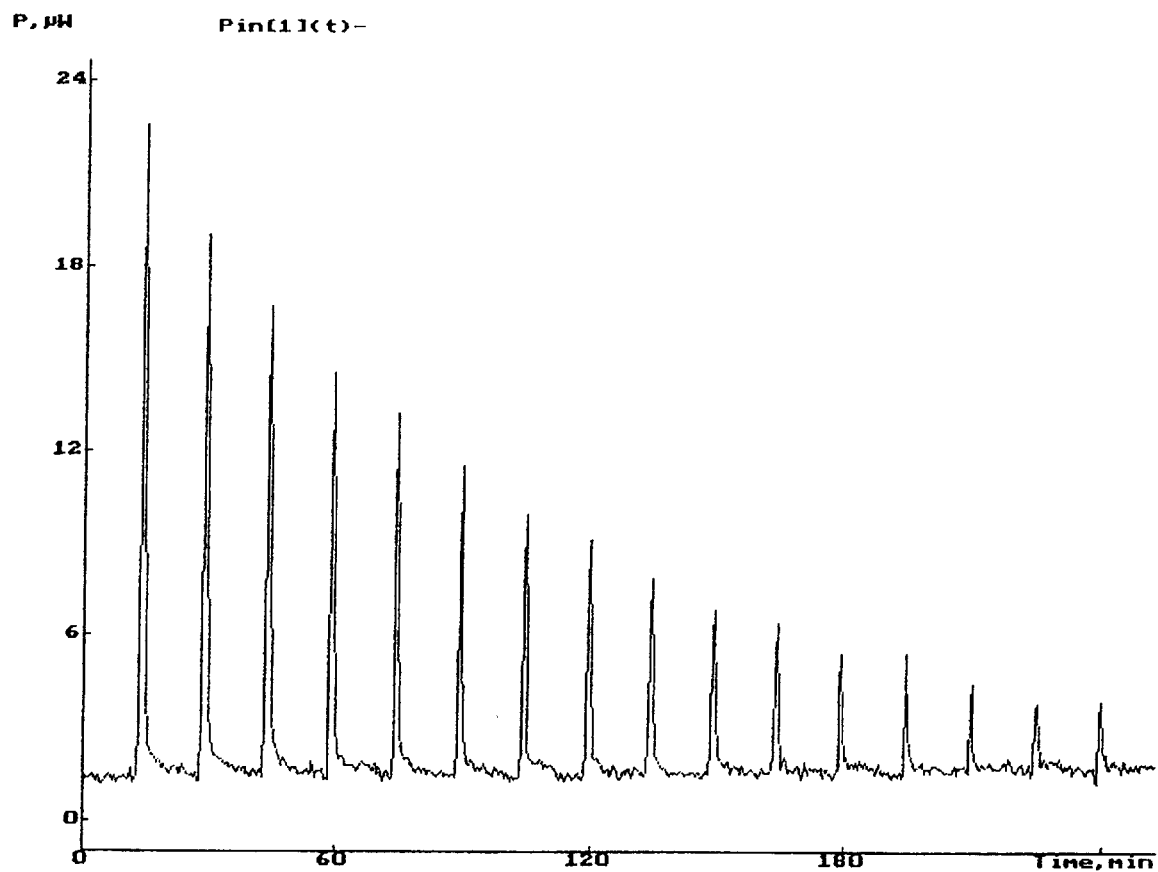

FIGS. 3a(1 of 2), 3a(2 of 2), 3b(1 of 2) and 3b(2 of 2) show an analysis of the ligand binding characteristics of the curves generated in FIG. 2;

FIG. 4 shows the $T_m$ plotted against the molar ratio showing the differences between PLL and NG23 binding in buffer and salt;

FIG. 5 shows the titration curve for herring sperm DNA (interaction of PAA with DNA);

FIG. 6 shows the results of a gel shift assay using NG30;

FIGS. 7A and 7B show gel shift assays using phosphorothioate oligonucleotide for both the random block copolymer NG32 (a) and the triblock copolymer NG33 (b);

FIGS. 8A and 8B show the results of microcalorimetry experiments using herring sperm DNA for both the random block copolymer NG32 (a) and the triblock copolymer NG33 (b).

Figure 9:
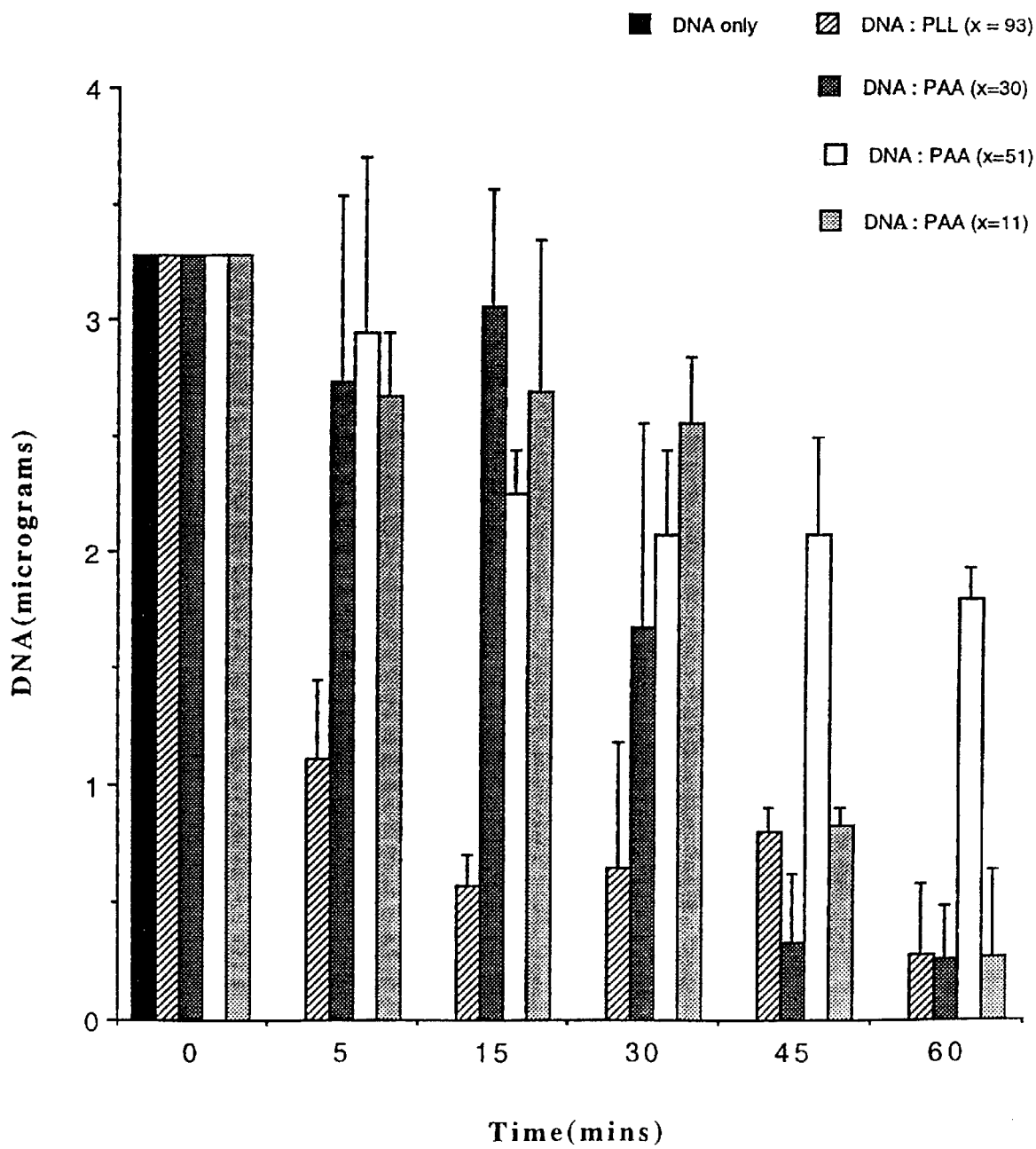

FIG. 9 shows the serum stability of DNA polycation complexes in comparison with free DNA. PLL=poly(L-lysine); PAA=bis acryloyl piperazine-2-methyl piperazine PAA; and x is the degree of polymerisation.

EXAMPLE 1

General Scheme for Polymers and Polymer Synthesis and Description of Analytical Methods used in Subsequent Examples Polyamidoamines Linear polyamidoamines are obtained by hydrogen transfer polyaddition reaction of primary monoamines (Scheme 1.a) or bis(secondary-amine)s (Scheme 1.b) to bisacrylamides [9]:

Scheme 1.a

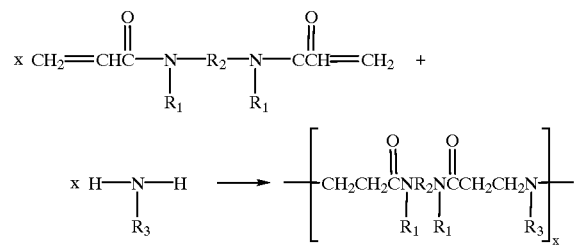

Scheme 1.b

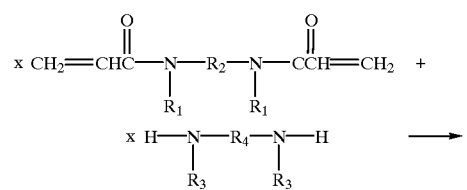

-continued

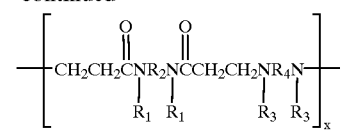

wherein x is from 1 to 70;
each $R_1$ is independently H or a linear or branched hydrocarbon chain —$C_nH_{2n+1}$ with n=1–4 whenever it occurs; each $R_2$ is independently a linear or branched alkylene chain —$C_nH_{2n}$— with n=1–4 whenever it occurs; and each $R_3$ is independently a linear or branched hydrocarbon chain —$C_nH_{2n+1}$ with n=1–4 whenever it occurs; each $R_4$ is independently a linear or branched alkylene chain —$C_nH_{2n}$— with n=2–4 whenever it occurs.

Preferably x is from 1 to 70.

Reference [9] is incorporated herein by reference.

1 mole of bisacrylamide and 1 mole of a primary monoamine or a secondary bisamine are mixed in the presence of water (about 2–4 ml/g of the sum of the monomers) or alcohols. It is advisable to add a small amount of radical inhibitor in order to avoid radical polymerization of the acrylic monomer. It is better to carry out the reaction under nitrogen atmosphere, but it is not strictly necessary. The preferred reaction temperatures range from 20 to 50° C. The reaction times vary from 1 to 7 days, depending on the reaction temperature and the nature of the monomers (steric hindrance on the aminic nitrogen greatly affects the polymerization rate). Isolation is usually performed by solvent/non solvent precipitation or ultrafiltration or dialysis in water. In order to increase the shelf stability of PAA's, it is better to transform them into their hydrochloride salts by acidification of the reaction mixture with diluted HCl before isolation.

Poly(amidoamine)-poly(ethylene glycol) Block Copolymers

Poly(amidoamine)-poly(ethylene glycol) block copolymers [12] are prepared by copolymerizing aminated PEG's, that is PEG's functionalized at both ends with secondary aminic units [12], with another amine, in the presence of a bisacrylamide. In practice, the amine, the aminated PEG and bisacrylamide are mixed together in the presence of water or alcohols, taking care flat the sum of the moles of amine and aminated PEG equals the moles of bisacrylamide. The reaction conditions are exactly the same as in the PAA synthesis. Isolation is usually performed by ultrafiltration or dialysis in water.

Reference [12] is incorporated herein by reference.

Poly(amidoamine)-poly(ethylene glycol) Triblock Copolymers

They are prepared by a two-step procedure involving:
a) synthesis of a polyamidoamine end-capped with acrylamido groups;
b) saturation of the latter by addition of PEG aminated at one end with secondary amino groups.

The first step is accomplished following the general procedure for the synthesis of PAA's, but using an excess of bisacrylamide. The proper excess is selected on the basis of the Flory's theory on stepwise polymerizations [13] in order to obtain a PAA roughly of the desired length. Reference [13] is incorporated herein by reference.

In the second step 2.1 moles of monoaminated PEG per mole of excess bisacrylamide are added to the reaction mixture together with the proper amount of solvent and allowed to react for 3–5 days under the same conditions. Isolation is usually performed by ultrafiltration or dialysis in water.

After isolation, the products have been characterized by gel permeation chromatography (GPC), intrinsic viscosity measurement and potentiometric titration.

GPC analysis has been run making use of TSK-GEL G3000 PW and TSK-GEL G4000 PW columns connected in series, using TRIS buffer pH 8.09 as mobile phase (flow: 1 ml/min) and a UV detector operating at 230 nm. From the GPC chromatograms the number- and weight-average molecular weights ($M_n$ and $M_w$, respectively) have been calculated starting from a calibration curve purposely calculated for PAA's [14]. Intrinsic viscosities have been measured at 30° C. in TRIS buffer pH 8.09 by means of Ubbelohde viscometers. Potentiometric titrations with HCl have been performed on copolymers in order to determine the percentage of PAA and the molecular weight of the PAA segments. Reference [14] is incorporated herein by reference.

Interaction of DNA with Cationic Polymers

The interaction of DNA with polyamidoamine polymers can be described in general terms by its interaction with oligonucleotides. In the experimental work presented here, a number of different DNA's have been used for characterisation. These are: a 15mer phosphorothioate oligonucleotide, Herring sperm DNA, a short chain length phosphodiester oligonucleotide of about 10–30 nucleotides length which is about 80% single stranded in nature, and calf thymus DNA which is double stranded phosphodiester DNA of high molecular weight. All work described below measures the relative amounts of binding between DNA and polymer by reference to the input DNA:polymer ratio calculated by DNA bases (or phosphate groups) per monomer of the polymer.

The medium in which the experiment is conducted has a significant effect on the interactions between DNA and polycations. Interactions are dependent upon the salt concentration, the buffer ion, and the pH of the ionisable groups. Experiments have therefore been carried out in various media to understand the effects which may be observed in biological fluids which are much less easy to measure.

A number of different techniques have been used to define the interactions between DNA and polycations. These include electrophoresis gel shift assays, isothermal titration microcalorimetry, determination of DNA melting points, circular dichroism (CD) and photon correlation spectroscopy (PCS).

Gel Shift Electrophoresis

If DNA is added to a central well on an agarose gel, and a potential difference applied to the gel, the DNA will migrate to the anode. If cationic polymer is applied it will migrate to the cathode. Complexes which are electrically neutral and or relatively large do not move from the central well. If complexes are incomplete, or are weakly bound they may migrate more slowly to either anode or cathode depending on overall charge of the complex. Electrophoresis is carried out in Tris borate buffer pH7.6.

Isothermal Titration Microcalorimetry

Virtually all chemical reactions and interactions results in either the liberation or abstraction of heat. With a sensitive enough calorimeter, these heat changes (enthalpies) can be measured even for small amounts of biological materials. Titrating one component against another by small additions from a microsyringe results in a series of heat outputs which reach zero when the reaction is complete. Analysis of the heat evolved over the titration can give measures of the strength of reaction, the equilibrium constants and other information about the complexation reaction. The results presented for isothermal titration microcalorimetry have been carried out in TBE buffer so they are directly comparable to the gel shift assays.

Determination of DNA Melting Points

When heat is applied to double stranded DNA, the DNA splits into single strands. The temperature at which this occurs depends on the base composition of the DNA, and is related to the strength of interaction of the two strands. This event can be readily measured by the accompanying increase in absorbance at 260 nm. The temperature at which 50% of the absorbance increase occurs (50% strand separation) is known as the melting temperature ($T_m$). The presence of cationic polymer binding to DNA can stabilise the DNA thus increasing the $T_m$. These assays have again been carried out in TBE.

Photon Correlation Spectroscopy (PCS)

The scattering of laser light by colloids can be analysed to provide an accurate measurement of the size of the colloids. This technique has been used to assess the size of some of the complexes studied.

The following Examples relate to the characterisation of interactions between DNA and polyamidoamines.

EXAMPLE 2

BPMP2 (Bisacryloyl piperazine-2 methyl piperazine) Copolymer

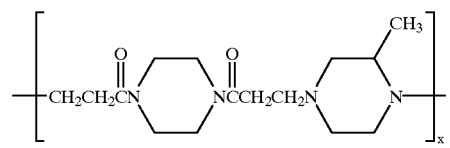

wherein x is 1 to 70.

Synthesis

Bisacryloyl piperazine (BAP) (2.718 g; 14.00 mmol) was dissolved into 0.1402 g/ml 2-methylpiperazine (2MP) aqueous solution (10.00 ml; 14.00 mmol); after addition of distilled water (5 ml), the reaction mixture was left for 5 days at 25° C. and, finally, freeze-dried. Yield: 3.58 g.

GPC retention time=825 sec. Intrinsic viscosity=0.45 dl/g. $M_w$=18000. $M_n$=9000.

Experimental

The interaction between polyamidoamines and DNA has been characterised mainly using a synthetic oligonucleotide 15mer with stable phosphorothioate linkages. These linkages are negatively charged as in the natural phosphodiester linked DNA. To establish the potential of PAA as a cationic polymer suitable for DNA delivery, these interactions have been compared to poly-L Lysine (PLL), the most studied of the cationic polymers used in DNA delivery.

In FIG. 1 a gel-shift assay is shown comparing the interaction of (a) poly-L-lysine (PLL) and (b) PAA with phosphorothioate oligonucleotide (15 mer) at various oligonucleotide:polymer ratios. The samples were applied to the central wells of an agarose gel and electrophoresed for 30 minutes at 50 volts. The poly-L-lysine complexes in FIG. 1a show either no uncomplexed DNA or polymer over a wide range of nucleotide to monomer ratios. This probably results from the co-operative binding activity seen between PLL and DNA. The PAA/DNA complex FIG. 1b, shows a small range of DNA:PAA ratios (1:1–1:2) where polymer and oligonucleotide appear to be completely complexed.

Figure 2A:
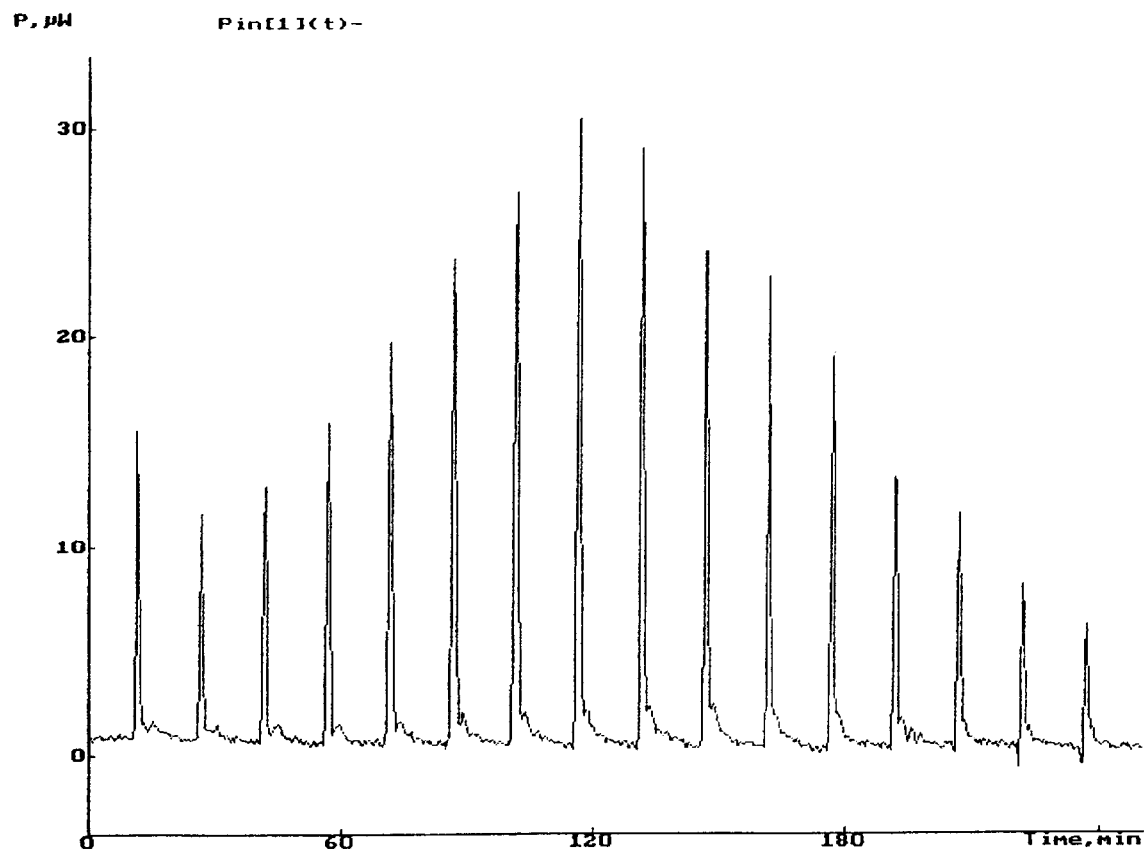
FIGS. 2A and 2B show the result of isothermal titration microcalorimetry experiments comparing the interactions between PAA and DNA (b) and poly-L-lysine and DNA (a)
Figure 2B:
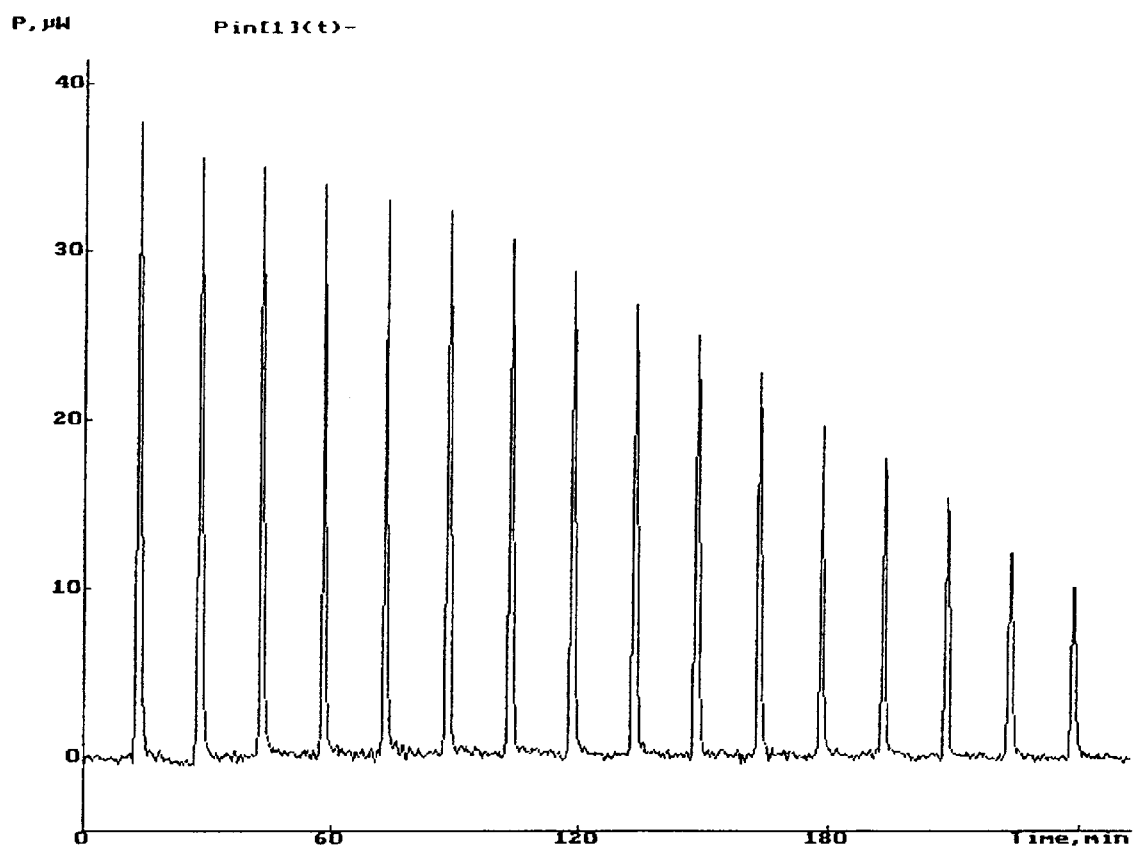

When these interactions were investigated using isothermal titration microcalorimetry, the net thermodynamic characteristics of the interaction can be seen following subtraction of the heat of dilution of the polymer from the titration of polymer into DNA. From these curves it can be seen that the interactions between PAA and DNA are different from those of poly-L lysine and DNA (FIGS. 2 & 3). With poly-L-lysine (FIG. 2a), interactions initially gave off smaller amounts of heat leading to a peak of heat output, and the reaction did not saturate so rapidly. These results strongly suggest co-operative binding. In contrast, PAA (FIG. 2b) showed a simpler profile of heat changes in which saturation was achieved more readily. This profile again appeared to be multiphasic. The ligand binding characteristics of these curves were analysed (FIGS. 3a and 3b). These showed that ligand binding with PLL appeared to be a triphasic process with interactions at nucleotide to monomer ratios of 0.5, 1.0 and 1.5. The first interaction was weakly exothermic, the second endothermic and the third more strongly exothermic. In contrast PAA gave a single exothermic interaction with DNA at an oligonucleotide to polymer ratio of 0.92. Overall the PAA reaction was more exothermic than the PLL reaction.

In the melting temperature experiments, sense and antisense oligonucleotide was mixed with polymer. In this mixture the sense and antisense strands will combine to give a double stranded piece of DNA interacting with the polymer. Again the change in $T_m$ was measured over a range of oligonucleotide to monomer ratios. In FIG. 4 the $T_m$ values resulting from interactions of various ratios of polymer to DNA were measured in TBE buffer. PLL showed an increasing stability of the oligonucleotide complex with increasing amounts of polymer, the most stable complexes being achieved with a large excess of polymer. PAA however showed a maximum stability at molar ratios of ON:Polymer between 1:1 and 2:1.

The interaction of PAA with DNA of a number of different types have been analysed by both gel-shift electrophoresis and isothermal titration microcalorimetry, and the interactions with herring sperm DNA and calf thymus DNA are similar to those seen for the phosphorothioate oligonucleotides. The titration curve for herring sperm DNA is shown in FIG. 5.

The particle size of the complexes will be very important in determining the biodistribution of the complexes in vivo. The size of the complexes produced under various conditions have been measured using photon correlation spectroscopy and can be found in Table 1. PLL complexes are usually insoluble after a 1:1 ratio (ie after charge neutralisation), whereas oligonucleotide:PAA complexes were soluble below saturating levels of polymer (ie 1:2 ON:polymer ratios). Generally, in buffer, aggregates with PLL are larger than those of PAA as measured by photon correlation spectroscopy (PCS). In water the PAA complexes are soluble and not detectable by PCS.

TABLE 1

Size of Oligonucleotide-Cationic Polymer Complexes measured by PCS.

| Polymer | Complex in water | Complex in TBE |
| --- | --- | --- |
| PLL | 198 nm | >3 µm |
| PAA | soluble | 250 nm |
| PAA-PEG/PEG-PAA-PEG | soluble | soluble |

EXAMPLE 3

Other Polyamidoamine Structures

Polyamidoamines of a wide variety of structures can be synthesised, which will vary in their physicochemical properties such as pK of the amide groups, and the spacing between the charged amide groups which will govern the interaction with DNA.

MBA-2MP (Methylene bisacrylamide-2methylpiperazine) copolymer

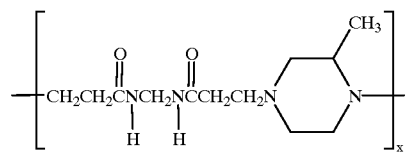

wherein x is 1 to 70.

Synthesis

N,N'Methylenebisacrylamide (MBA) (1.177 g; 7.63 mmol) was suspended in 0.0780 g/ml 2MP aqueous solution (10.00 ml; 7.79 mmol) in the presence of 4-methoxyphenol (6 mg); the reaction mixture was stirred at 20° C., under nitrogen atmosphere and in the dark, for 4 days. Afterwards, HCl was added up to pH 2–3 and the resulting solution was ultrafiltered in water through a membrane with $M_w$ cut off 3000 and freeze-dried. Yield=1.30 g. GPC retention time 890 sec. Intrinsic viscosity=0.24 dl/g. $M_w$=8500. $M_n$=5300.

MBA-MMA (Methylene bisacrylamide-methylamine) Copolymer

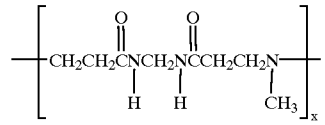

wherein x is 1 to 70.

Synthesis

MBA (1.668 g; 10.82 mmol) was suspended in 0.0343 g/ml methylamine aqueous solution (10.00 ml; 11.04 mmol) in the presence of 4-methoxyphenol (8 mg); the reaction mixture was stirred at 20° C., under nitrogen atmosphere and in the dark, for 4 days. Afterwards, HCl was added up to pH 2–3 and the resulting solution was ultrafiltered in water through a membrane with $M_w$ cut off 3000 and freeze-dried. Yield=0.93 g. GPC retention time=875 sec. Intrinsic viscosity=0.24 dl/g. $M_w$=9500. $M_n$=6000.

MBA-DMEDA (Methylene bis acrylamide-dimethylethylene diamine) Copolymer

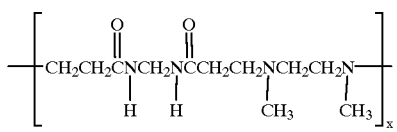

wherein x is 1 to 70.
Synthesis

MBA (1.980 g; 12.84 mmol) was suspended in 0.148 g/ml N,N'-dimethylethylenediamine aqueous solution (7.51 ml; 12.58 mmol) in the presence of 4-methoxyphenol (11 mg); the reaction mixture was stirred at 25° C., under nitrogen atmosphere and in the dark, for 4 days. Afterwards, HCl was added up to pH 2–3 and the resulting solution was ultrafiltered in water through a membrane with $M_w$ cut off 3000 and freeze-dried. Yield=2.80 g. GPC retention time=780 sec. Intrinsic viscosity=0.53 dl/g. $M_w$=21500. $M_n$=9500.

Experimental

The binding properties of several different structures have been tested for their association with DNA by the gel shift assay. All of the above structures demonstrated an association with DNA which was similar to that seen with NG23. An example of one of these gels using NG30 is shown in FIG. 6.

Two different types of PEG-polyamidoamine copolymers have been synthesised. Firstly a random block copolymer (NG32), and secondly a triblock copolymer (NG33). These are described in Examples 4 and 5.

EXAMPLE 4

PEG-BP2MP2[Polyethylene glycol-(Bisacryloyl piperazine-2 methyl piperazine)] Block Copolymers
NG32=PEG BP2 MP2
Structure

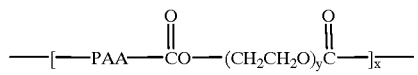

where:
the number y is about 45 and x is 1 to 70.
—PAA— is:

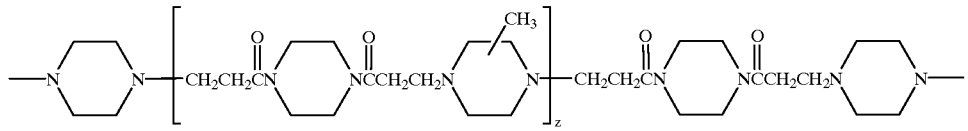

and the number z is about 6.6.

Synthesis 1,4-Bis(acryloyl)piperazine (1.003 g, 5.16 mmol), 2-methylpiperazine (0.455 g, 4.54 mmol), piperazinyl formate of PEG 2000 (1.536 g, 0.69 mmol), prepared as described in [18], and 4-methoxyphenol (5 mg) were dissolved in distilled water (5 ml) and allowed to stand at 25° C., under inert atmosphere and in the dark, for 3 days. After ultrafiltration in water through a membrane with $M_w$ cut off 10,000 the solution was freeze-dried. Yield=1.93 g. GPC retention time=785 sec. Intrinsic viscosity=0.55 dl/g. $M_w$=36000. $M_n$=10000. Percentage of PAA=53% (w/w). $M_n$ of the PAA segments=2300.

EXAMPLE 5

PEG-BP2MP-PEG [PEG-(Bisacryloyl piperazine-2 methyl piperazine)-PEG Triblock Copolymers
NG33=PEG-BP2MP-PEG
Structure

where:
the number y is about 43
—PAA— is:

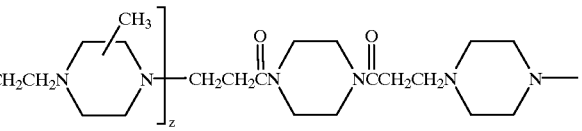

and the number z is about 6.7.

Synthesis 1,4-Bis(acryloyl)piperazine (1.081 g, 5.56 mmol), 2-methylpiperazine (0.491 g, 4.90 mmol) and 4-methoxyphenol (7 mg) were dissolved in distilled water (4 ml). The resulting solution was left at 25° C., under inert atmosphere and in the dark, for 2 days, then piperazinyl formate of PEG 1900 monomethyl ether (2.978 g, 1.47 mmol), prepared as described in [18], and distilled water (20 ml) were added, and the reaction mixture allowed to react for further 4 days under the same conditions. Finally, the solution was ultrafiltered through a membrane with $M_w$ cut off 10,000 and freeze-dried. Yield=2.85 g. GPC retention time=875 sec. Intrinsic viscosity=0.20 dl/g. $M_w$=11400. $M_n$=3300. Percentage of PAA=37% (w/w). $M_n$ of the PAA segments=2350.

Experimental

Both gel shift assays (FIG. 7) using phosphorothioate oligonucleotide and microcalorimetric titration analysis (FIG. 8) using herring sperm DNA are presented for both the random block copolymer NG32 (a) and the triblock copolymer NG33 (b). If it is assumed that the DNA interacts with the PAA but not the PEG moiety, the interaction appears to be identical to that of the PAA alone and therefore complexation was unaffected by the addition of a PEG moiety.

Photon correlation spectroscopy (Table 1 in Example 2) could not detect the presence of particles in either of the PAA-PEG complexes at any ratios of oligonucleotide to polymer, in either buffer or water. This is believed to be of great significance for DNA delivery.

EXAMPLE 6

Summary of Findings for Interaction of PAAs with Oligonucleotides

These polymers have been shown to interact with DNA in a different way to that described for other linear cationic polymers such as poly-L-lysine to form complexes with improved properties for DNA delivery systems. Binding is not co-operative, is pH dependent over a lower range than that seen with polymers of primary amines such as PLL. The binding of PAA to DNA is not co-operative in nature occurring over a more defined range of nucleotide to monomer ratios. Below the pK of the polymers the binding is stronger for PAA than that described for PLL, also the complexes with PAA are more soluble than those seen for PLL, and the PEG-PAA polymers appear to be soluble at all nucleotide to monomer ratios. Either as a repeating block copolymer structure or as an ABA block copolymer structure, inclusion of PEG into the polymer improves the solubility of the complex without affecting the binding of DNA to the polymer. Complexation is observed with both natural (phosphodiester) and synthetic (phosphorothioate) DNA for a range of polyamidoamine structures.

EXAMPLE 7

PEG—PAA—PEG-1

Structure

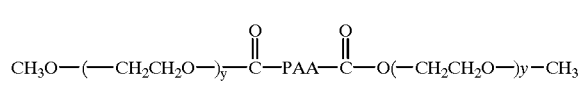

where:

the number y is about 43

—PAA— is:

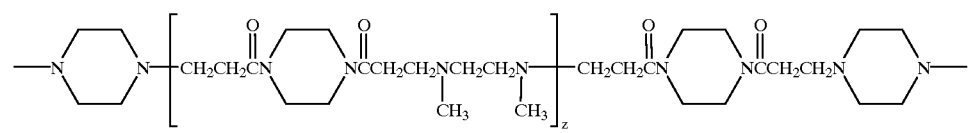

and the number z is about 6.4.

Synthesis

It was prepared by the same procedure as NG33, substituting N,N'-dimethylethylene diamine (0.527 ml; 4.90 mmol) for 2-methylpiperazine. Yield=2.74 g. GPC retention time=880 sec. Intrinsic viscosity=0.18 dl/g. $M_w$=10300. $M_n$=3500. Percentage of PAA=36% (w/w). $M_n$ of the PAA segments 2170.

EXAMPLE 8

PEG—PAA—PEG-II

Structure

where:

the number y is about 43

—PAA— is:

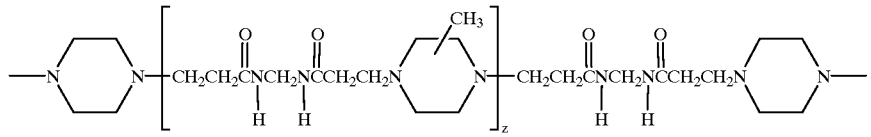

and the number z is about 4.2.

Synthesis

It was prepared by the same procedure as NG33, substituting N,N'-methylenebisacrylamide (0.922 g; 5.98 mmol) for 1,4-bis(acryloyl)piperazine. Yield=3.08 g. GPC retention time=890 sec. Intrinsic viscosity=0.15 dl/g. $M_w$=9600. $M_n$=2500. Percentage of PAA=26% (w/w). $M_n$ of the PAA segments=1350.

EXAMPLE 9

PEG—PAA—PEG-III

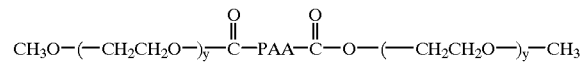

where:

the number y is about 113

—PAA— is:

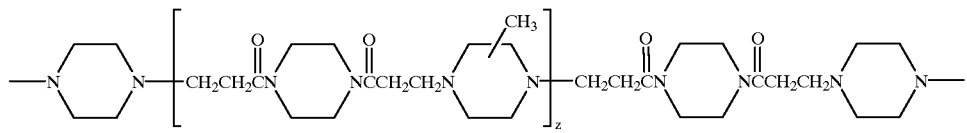

and the number z is about 6.3.

Synthesis

It was prepared by the same procedure as NG33, substituting piperazinyl formate of PEG 5000 monomethylether (7.534 g, 1.47 mmol), prepared as described in [18], for piperazinyl formate of PEG 1900 monomethylether. Yield=3.83 g. GPC retention time=840 sec. Intrinsic viscosity=0.30 dl/g. $M_w$=25000. $M_n$=8000. Percentage of PAA=18% (w/w). $M_n$ of the PAA segments=2200.

EXAMPLE 10

PEG—PAA-I

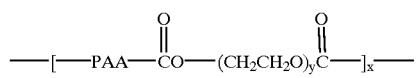

where:
the number y is about 45
—PAA— is:

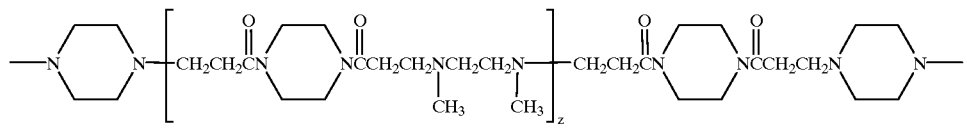

and the number z is about 6.9.

Synthesis:

It was prepared by the same procedure as NG32, substituting N,N'-dimethylethylene diamine (0.489 ml; 4.54 mmol) for 2-methylpiperazine. Yield=2.12 g. GPC retention time=780 sec. Intrinsic viscosity=0.58 dl/g. $M_w$=42000. $M_n$=11500. Percentage of PAA=54% (w/w). $M_n$ of the PAA segments=2310.

EXAMPLE 11

PEG—PAA-II

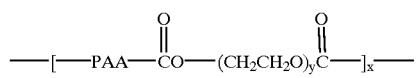

where:
the number y is about 45 and x is 1 to 70.
—PAA— is:

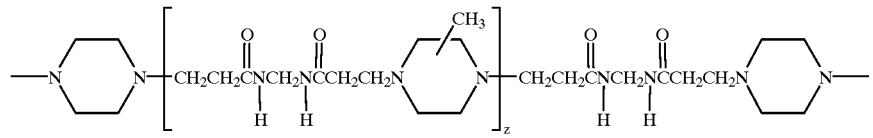

and the number z is about 4.3.

Synthesis

It was prepared by the same procedure as NG32, substituting N,N'-methylenebisacrylamide (0.854 g; 5.54 mmol) for 1,4-bis(acryloyl)piperazine. Yield=1.83 g. GPC retention time=795 sec. Intrinsic viscosity=0.49 dl/g. $M_w$=34000. $M_n$=10500. Percentage of PAA=42% (w/w). $M_n$ of the PAA segments=1420.

EXAMPLE 12

PEG—PAA-III

Structure

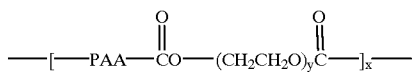

where:
the number y is about 90 and x is 1 to 70.
—PAA— is:

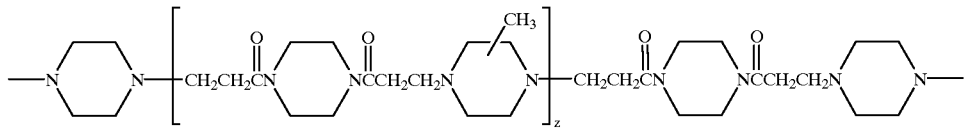

and the number z is about 6.5.

Synthesis

It was prepared by the same procedure as NG32, substituting piperazinyl formate of PEG 4000 (2.915 g, 0.69 mmol), prepared as described in [18], for piperazinyl formate of PEG 2000. Yield=2.94 g. GPC retention time=760 sec. Intrinsic viscosity=0.64 dl/g. $M_w$=58000. $M_n$=16000. Percentage of PAA=36% (w/w). $M_n$ of the PAA segments= 2250.

EXAMPLE 13

Administration of Ha-ras Antisense Sequence to T24 Bladder Carcinoma Cells

Polymer NG23 (PAA—PEG) is mixed with Ha-ras antisense oligonucleotide to form a polymer-oligonucleotide composition as in the previous Examples.

The composition is added to T24 bladder carcinoma cells growing in culture.

This leads to a reduction in viability of the cells and an inhibition of Ha-ras protein production.

EXAMPLE 14

Transfection of Mammalian Cells with a Chloramphenicol Acetyl Transferase (CAT) Gene-containing Plasmid Polymer NG23 (PAA—PEG) is mixed with a plasmid which expresses the CAT gene in mammalian cells to form a polymer-DNA composition as in the previous Examples.

The composition is added to suitable mammalian cells growing in culture. The cells are transfected by the plasmid and CAT gene expression is measured using standard methods with $^{14}$C-labelled chloramphenicol.

EXAMPLE 15

Administration of CFTR (Cystic Fibrosis Transmembrane Regulator) cDNA to a Cystic Fibrosis Patient Polymer NG23 (PAA—PEG (which has been manufactured and kept under sterile conditions) is mixed with sterile and pyrogen-free plasmid DNA encoding, and capable of expressing in human lung cells, the CFTR cDNA. The resulting composition is prepared into a sterile, pyrogen free formulation suitable for administration to the lungs. An effective amount of the formulation is administered to the lungs of the CF patient.

EXAMPLE 16

Serum Stability of DNA Polycationic Complexes in Comparison with Free DNA

A DNA plasmid (PCT0297L, 30 μg) was mixed at optimal ratios with polymers (DNA:PAA, 1:2, DNA:PLL 1:1.5) to form a DNA polycation complex. The complex was then added to newborn calf serum and incubated for various time periods (total volume 100 μl, 64% serum) at 37° C. After incubation the samples (10 μl) were snap frozen to prevent further degradation, and when all samples had been taken, were loaded onto an agarose electrophoresis gel prestained with ethidium bromide. The gel buffer was a NaOH/KCl/EDTA system pH 12.5 which allowed the complex to dissociate and the DNA to separate according to molecular weight. The bands were visualised using a UV light box recorded using a CCD camera and the images scanned using a Shimadzu densitometer at 550 nm to give a quantitative estimate of the amount of undegraded plasmid in comparison to untreated complex.

The results are shown in FIG. 9. Free DNA is degraded within 5 minutes in this system. A poly-L-lysine complex has some protective effect, but is not as effective as complexes with polyamidoamines. We note from this work that polyamidoamines with a higher degree of polymerisation are more effective in protecting from degradation.

REFERENCES

[1] R. G. Crystal (1995) *Science* 270, 404.
[2] L. Ledoux (1965) *Prog. Nucl. Acid. Res.* 4, 231.
[3] R. T. Fraley, C. S. Fornari and S. Kaplan (1979) *Proc. Natl. Acad. Sci. USA* 76, 3348.
[4] L. Felgner, T. R. Gadek, M. Holm, R. Roman, H. W. Chan, M. Wenz, J. P. Northrop, G. M. Ringold and M. Danielsen (1987) *Proc. Natl. Acad. Sci. USA* 84, 7413.
[5] F. E. Farber, J. L. Melnick and J. S. Butel (1975) *Biochim. Biophys. Acta* 390, 298.
[6] E. Wagner, M. Zenke, M. Cotten, H. Beug and M. L. Birnstiel (1990) *Proc. Natl. Acad. Sci. USA* 87, 3410.
[7] C. Plank, B. Oberhauser, K. Mechtler, C. Koch and E. Wagner (1994) *J. Biol. Chem.* 269, 12918.
[8] J-P. Clarenc, G. Degols, J. P. Leonetti, P. Milhaud and B. Lebleu (1993) *Anticancer Drug Design* 8, 81.
[9] P. Ferruti, R. Barbucci and M. A. Marchisio (1985) *Polymer* 26, 1336.
[10] J. Haensler and F. C. Szoka (1993) Bioconjugate Chem. 4, 372–379.
[11] M. L. Nucci, R. Shorr and A. Abuchowski (1991) *Adv. Drug Del. Rev.* 6, 133.
[12] E. Ranucci and P. Ferruti (1991) *Macromolecules* 24, 3747.
[13] P. J. Flory, "Principles of Polymer Chemistry", Cornell University Press, Ithaca, N.Y. (1953).
[14] F. Bignotti, P. Sozzani, E. Ranucci and P. Ferruti (1994) *Macromolecules* 27, 7171.
[15] E. Ranucci, G. Spagnoli, P. Ferruti, D. Sgouras and R Duncan (1991) *J. Biomater. Sci. Polymer Edn* 2, 303–315.
[16] R. Duncan, P. Ferruti, D. Sgouras, A. Tuboku-Metzger, E. Ranucci and F. Bignotti (1994) *J. Drug Targeting* 2, 341–347.
[17] S. Katayose and K. Kataoka (1994) Salt Lake City Symposium of the Controlled Release Society (Abstract).

[18] E. Ranucci and P. Ferruti (1990) *Synthetic Commun.* 20, 2951.

Key to Polymer Codes and Structures

NG23=BPMP2 (Bisacryloylpiperazine-2 methyl piperazine)
NG28=MBA-2MP (Methylenebisacrylamide-2 methyl piperazine)
NG29=MBA-MMA (Methylenebisacrylamide-methylamine)
NG30=MBA-DMEDA (Methylenebisacrylamidedimethylethylene diamine)
NG32=PEG BP2MP2 (Polyethyleneglycol-(Bisacryloyl-piperazine-2 methylpiperazine) block copolymer
NG33=PEG BP2MP2-PEG triblock copolymer

ABBREVIATIONS

PAA is poly(amidoamine); PLL is poly(-L-lysine); PEG is poly(ethyleneglycol).

We claim:

1. A composition for delivering a nucleic acid, the composition comprising
    a linear polymer with a backbone comprising amido and tertiary amino groups arranged regularly on the backbone, and
    a nucleic acid bound to the polymer.

2. The composition of claim 1 wherein the linear polymer comprises a poly(amidoamine).

3. The composition of claim 2 wherein the poly(amidoamine) has a formula selected from the group consisting of:

wherein z is from 1 to 70 and each $R_1$ is independently H or a linear or branched hydrocarbon chain —$C_nH_{2n+1}$ with n=1–4 whenever it occurs;

wherein each $R_2$ is independently a linear or branched alkylene chain —$C_nH_{2n}$— with n=1–4 whenever it occurs;

wherein each $R_3$ is independently a linear or branched hydrocarbon chain —$C_nH_{2n+1}$ with n=1–4 whenever it occurs;

wherein each $R_4$ is independently a linear or branched alkylene chain —$C_nH_{2n}$— with n=2–4 whenever it occurs;

wherein each $R_5$ is independently a linear or branched hydrocarbon chain —$C_nH_{2n+1}$ with n=1–4;

wherein each $R_6$ is independently a linear or branched alkylene chain —$C_nH_{2n}$— with n=2–4;

and wherein $R_7$, $R_8$, $R_9$ and $R_{10}$ are independently H or a linear or branched hydrocarbon chain —$C_nH_{2n+1}$ with n=1–3 whenever they occur.

4. The composition of claim 2 wherein the poly(amidoamine) has a formula selected from the group consisting of

[(a)]

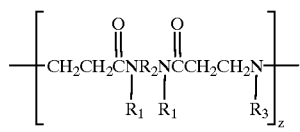

or

[(b)]

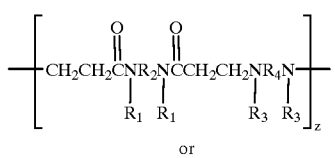

or

[(c)]

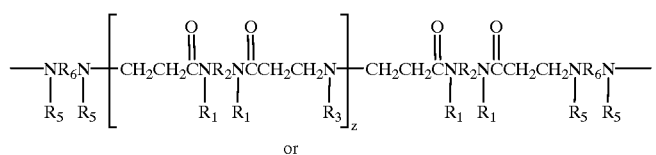

or (d)

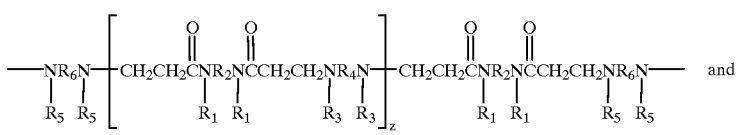 and

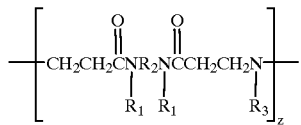

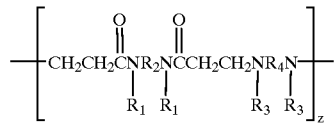

and

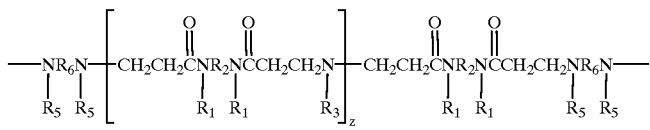

wherein at least one of the substituents selected from the group consisting of

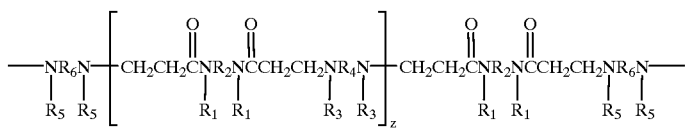

is replaced by

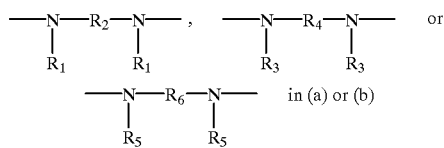

wherein z is from 1 to 70 and each $R_1$ is independently H or a linear or branched hydrocarbon chain —$C_nH_{2n+1}$ with n=1–4 whenever it occurs;

wherein each $R_2$ is independently a linear or branched alkylene chain —$C_nH_{2n}$— with n=1–4 whenever it occurs;

wherein each $R_3$ is independently a linear or branched hydrocarbon chain —$C_nH_{2n+1}$ with n=1–4 whenever it occurs;

wherein each $R_4$ is independently a linear or branched alkylene chain —$C_nH_{2n}$— with n=2–4 whenever it occurs;

wherein each $R_5$ is independently a linear or branched hydrocarbon chain —$C_nH_{2n+1}$ with n=1–4;

wherein each $R_6$ is independently a linear or branched alkylene chain —$C_nH_{2n}$— with n=2–4;

and wherein $R_7$, $R_8$, $R_9$ and $R_{10}$ are independently H or a linear or branched hydrocarbon chain —$C_nH_{2n+1}$ with n=1–3 whenever they occur.

5. The composition of claim 1 wherein the linear polymer consists of a poly(amidoamine).

6. The composition of claim 1 wherein the linear polymer further comprises ethylene glycol or poly(ethylene glycol).

7. The composition of claim 6 wherein the linear polymer is a poly(ethylene glycol)-poly(amidoamine) block copolymer or an ethylene glycol-poly(amidoamine) block copolymer.

8. The composition of claim 7 wherein the linear polymer is a block copolymer with the structure

[poly(amidoamine)-(ethylene glycol)$_y$]$_x$ wherein x is from 1 to 50 and each y is independently from 1 to 200 whenever it occurs.

9. The composition of claim 7 wherein the linear polymer is a block copolymer with the structure (ethylene glycol)y-poly(amidoamine)-(ethylene glycol)$_y$ wherein each y is independently from 1 to 200.

10. The composition of claim 6 wherein the linear polymer has the formula

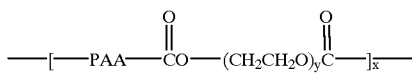

wherein PAA is a poly(amidoamine) and wherein x is from 1 to 50 and y is from 1 to 200.

11. The composition of claim 10 wherein the poly(amidoamine) has a formula selected from the group consisting of:

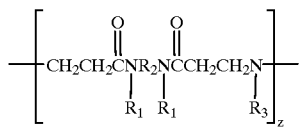

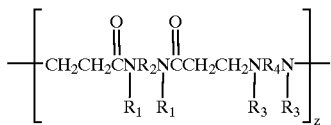

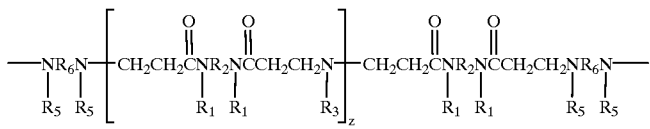

and

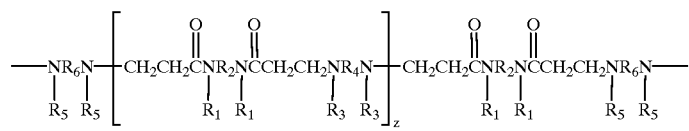

wherein z is from 1 to 70 and each $R_1$ is independently H or a linear or branched hydrocarbon chain $-C_nH_{2n+1}$ with n=1–4 whenever it occurs;

wherein each $R_2$ is independently a linear or branched alkylene chain $-C_nH_{2n}-$ with n=1–4 whenever it occurs;

wherein each $R_3$ is independently a linear or branched hydrocarbon chain $-C_nH_{2n+1}$ with n=1–4 whenever it occurs;

wherein each $R_4$ is independently a linear or branched alkylene chain $-C_nH_{2n}-$ with n=2–4 whenever it occurs;

wherein each $R_5$ is independently a linear or branched hydrocarbon chain $-C_nH_{2n+1}$ with n=1–4;

wherein each $R_6$ is independently a linear or branched alkcylene chain $-C_nH_{2n}-$ with n=2–4;

and wherein $R_7$, $R_8$, $R_9$, and $R_{10}$ are independently H or a linear or branched hydrocarbon chain $-C_nH_{2n+1}$ with n=1–3 whenever they occur.

12. The composition of claim 10 wherein the poly(amidoamine) has a formula selected from the group consisting of

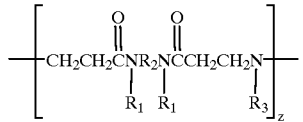

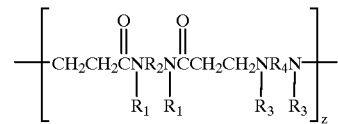

and

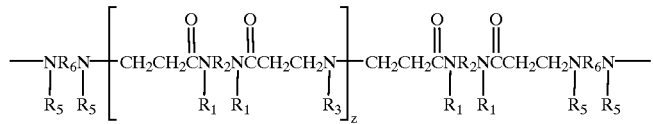

wherein at least one of the substituents selected from the group consisting of

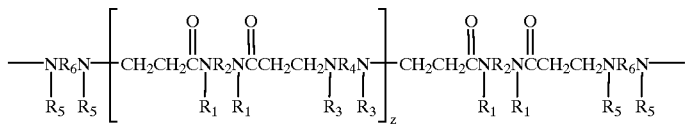

is replaced by

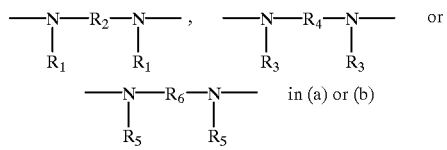

wherein z is from 1 to 70 and each $R_1$ is independently H or a linear or branched hydrocarbon chain —$C_nH_{2n+1}$ with n=1–4 whenever it occurs;

wherein each $R_2$ is independently a linear or branched alkylene chain —$C_nH_{2n}$— with n=1–4 whenever it occurs;

wherein each $R_3$ is independently a linear or branched hydrocarbon chain —$C_nH_{2n+1}$ with n=1–4 whenever it occurs;

wherein each $R_4$ is independently a linear or branched alkylene chain —$C_nH_{2n}$— with n=2–4 whenever it occurs;

wherein each $R_5$ is independently a linear or branched hydrocarbon chain —$C_nH_{2n+1}$ with n=1–4;

wherein each $R_6$ is independently a linear or branched alkylene chain —$C_nH_{2n}$— with n=2–4;

and wherein $R_7$, $R_8$, $R_9$ and $R_{10}$ are independently H or a linear or branched hydrocarbon chain —$C_nH_{2n+1}$ with n=1–3 whenever they occur.

13. The composition of claim 6 wherein the linear polymer has the formula

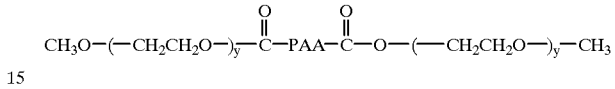

wherein PAA is a poly(amidoamine) and y is from 1 to 200.

14. The composition of claim 13 wherein the poly(amidoamine) has a formula selected from the group consisting of:

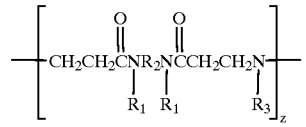

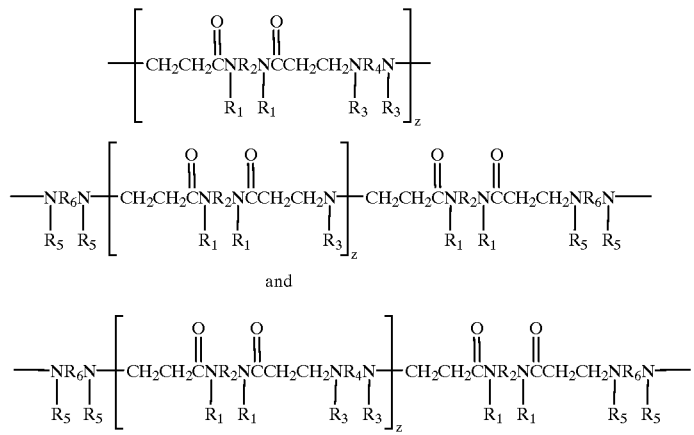

and wherein z is from 1 to 70 and each $R_1$ is independently H or a linear or branched hydrocarbon chain —$C_nH_{2n+1}$ with n=1–4 whenever it occurs;

wherein each $R_2$ is independently a linear or branched alkylene chain —$C_nH_{2n}$— with n=1–4 whenever it occurs;

wherein each $R_3$ is independently a linear or branched hydrocarbon chain —$C_nH_{2n+1}$ with n=1–4 whenever it occurs;

wherein each $R_4$ is independently a linear or branched alkylene chain —$C_nH_{2n}$— with n=2–4 whenever it occurs;

wherein each $R_5$ is independently a linear or branched hydrocarbon chain —$C_nH_{2n+1}$ with n=1–4;

wherein each $R_6$ is independently a linear or branched alkylene chain —$C_nH_{2n}$— with n=2–4;

and wherein $R_7$, $R_8$, $R_9$, and $R_{10}$ are independently H or a linear or branched hydrocarbon chain —$C_nH_{2n+1}$ with n=1–3 whenever they occur.

15. The composition of claim 13 wherein the poly(amidoamine) has a formula selected from the group consisting of

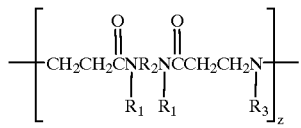

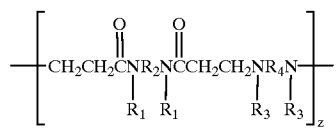

and

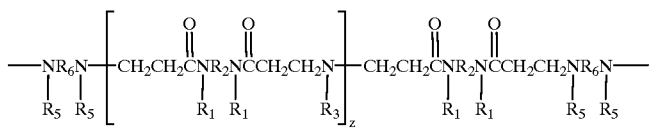

wherein at least one of the substituents selected from the group consisting of

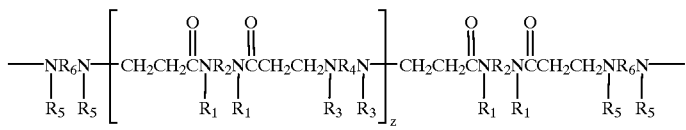

is replaced by

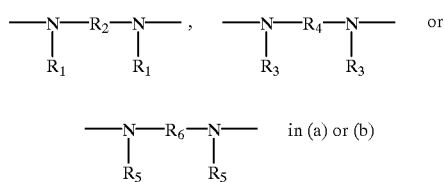

wherein z is from 1 to 70 and each $R_1$ is independently H or a linear or branched hydrocarbon chain —$C_nH_{2n+1}$ with n=1–4 whenever it occurs;
wherein each $R_2$ is independently a linear or branched alkylene chain —$C_nH_{2n}$— with n=1–4 whenever it occurs;
wherein each $R_3$ is independently a linear or branched hydrocarbon chain —$C_nH_{2n+1}$ with n=1–4 whenever it occurs;
wherein each $R_4$ is independently a linear or branched alkylene chain —$C_nH_{2n}$— with n=2–4 whenever it occurs;

wherein each $R_5$ is independently a linear or branched hydrocarbon chain —$C_nH_{2n+1}$ with n=1–4;
wherein each $R_6$ is independently a linear or branched alkylene chain —$C_nH_{2n}$— with n=2–4;
and wherein $R_7$, $R_8$, $R_9$ and $R_{10}$ are independently H or a linear or branched hydrocarbon chain —$C_nH_{2n+1}$ with n=1–3 whenever they occur.

16. The composition of claim 1 wherein the nucleic acid is DNA.

17. The composition of claim 1 wherein the nucleic acid comprises a phosphorothioate linkage.

18. The composition of claim 1 wherein the nuclcic acid is RNA.

19. The composition of claim 18 wherein the nucleic acid derivative comprises a phosphorothioate linkage.

20. The composition of claim 1 wherein the polymer further comprises a biological recognition signal material.

21. A method of making the composition of claim 1, the method comprising contacting the nucleic acid with the linear polymer.

22. The composition of claim 1 wherein the nucleic acid is an antisenise nucleic acid.

23. The composition of claim 1 wherein the nucleic acid is an oligonucleotide.

24. The composition of claim 23 wherein the oligonucleotide is an antisense oligonucleotide.

25. The composition of claim 23 wherein the oligonucleotide has been modified by replacing one or more of the naturally occurring phosphodiester linkages with another linkage.

26. A composition comprising
(a) a linear polymer with a backbone comprising amido and tertiary amino groups arranged regularly on the backbone;
(b) a nucleic acid bound to the polymer; and
(c) a pharmaceutically acceptable carrier.

27. A method of delivering a nucleic acid to a host, the method comprising administering to said host an effective amount of a composition comprising a linear polymer with a backbone comprising amido and tertiary amino groups arranged regularly on the backbone, wherein the nucleic acid is bound to the backbone.

28. A method of delivering a nucleic acid to a cell in an environment, the method comprising administering to the environment a composition comprising a linear polymer with a backbone comprising amido and tertiary amino groups arranged regularly on the backbone, wherein the nucleic acid is bound to the backbone,
wherein the environment is a human, other animal, or culture medium.

29. The method of claim 28 wherein the composition is contacted with the cell.

30. A polymer with the formula (ethylene glycol)$_y$-poly(amidoamine)-(ethyleneglycol)$_y$,
wherein each y is independently from 1 to 200.

31. The polymer of claim 30 with the formula

wherein PAA is a poly(amidoamine) and y is from 1 to 200.

32. The polymer of claim 31 wherein the poly(amidoamine) has a formula selected from the group consisting of:

wherein z is from 1 to 70 and each $R_1$ is independently H or a linear or branched hydrocarbon chain $-C_nH_{2n+1}$ with n=1–4 whenever it occurs;

wherein each $R_2$ is independently a linear or branched alkylene chain $-C_nH_{2n}-$ with n=1–4 whenever it occurs;

wherein each $R_3$ is independently a linear or branched hydrocarbon chain $-C_nH_{2n+1}$ with n=1–4 whenever it occurs;

wherein each $R_4$ is independently a linear or branched alkylene chain $-C_nH_{2n}-$ with n=2–4 whenever it occurs;

wherein each $R_5$ is independently a linear or branched hydrocarbon chain $-C_nH_{2n+1}$ with n=1–4;

wherein each $R_6$ is independently a linear or branched alkylene chain $-C_nH_{2n}-$ with n=2–4;

and wherein $R_7$, $R_8$, $R_9$, and $R_{10}$ are independently H or a linear or branched hydrocarbon chain $-C_nH_{2n+1}$ with n=1–3 whenever they occur.

33. The polymer of claim 31 wherein the poly(amidoamine) has a formula selected from the group consisting of

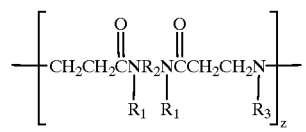

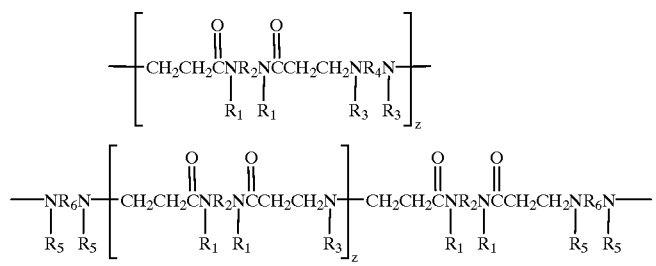

and

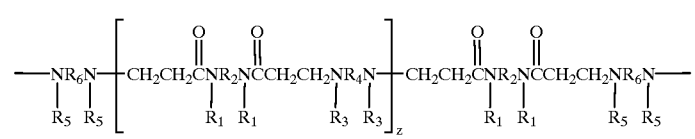

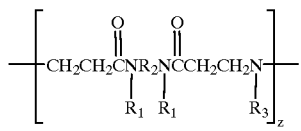

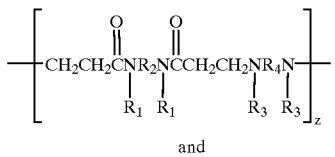

and

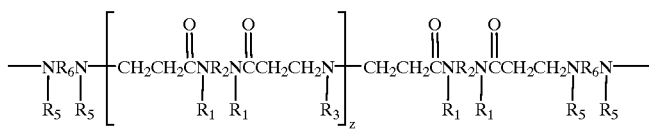

wherein at least one of the substituents selected from the group consisting of

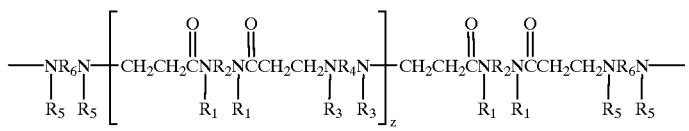

is replaced by

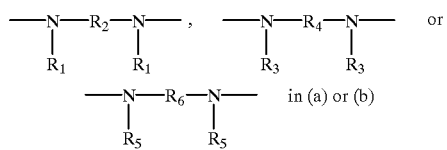

wherein z is from 1 to 70 and each $R_1$ is independently H or a linear or branched hydrocarbon chain —$C_nH_{2n+1}$ with n=1–4 whenever it occurs;

wherein each $R_2$ is independently a linear or branched alkylene chain —$C_nH_{2n}$— with n=1–4 whenever it occurs;

wherein each $R_3$ is independently a linear or branched hydrocarbon chain —$C_nH_{2n+1}$ with n=1–4 whenever it occurs;

wherein each $R_4$ is independently a linear or branched alkylene chain —$C_nH_{2n}$— with n=2–4 whenever it occurs;

wherein each $R_5$ is independently a linear or branched hydrocarbon chain —$C_nH_{2n+1}$ with n=1–4;

wherein each $R_6$ is independently a linear or branched alkylene chain —$C_nH_{2n}$— with n=2–4;

and wherein $R_7$, $R_8$, $R_9$ and $R_{10}$ are independently H or a linear or branched hydrocarbon chain —$C_nH_{2n+1}$ with n=1–3 whenever they occur.

34. A method of treating a patient suffering from cancer comprising administering to the patient an effective amount of a composition comprising a linear polymer with a backbone comprising amido and tertiary amino groups arranged regularly on the backbone and a nucleic acid bound to the polymer that encodes a molecule having a cytotoxic function.

35. The method of claim 34 comprising
administering to the patient an effective amount of a composition comprising a linear polymer with a backbone comprising amido and tertiary amino groups arranged regularly on the backbone and a nucleic acid bound to the polymer that encodes a cytosine deaminase; and
concomitantly administering 5-fluorocytosine to the patient.

36. A method of treating a patient suffering from cancer comprising administering to the patient an effective amount of a composition comprising a linear polymer with a backbone comprising amido and tertiary amino groups arranged regularly on the backbone and a nucleic acid bound to the polymer that encodes a ribozyme that is capable of cleaving RNA or DNA.

* * * * *